United States Patent
Hannaford et al.

(10) Patent No.: US 10,092,355 B1
(45) Date of Patent: Oct. 9, 2018

(54) BIOPHOTONIC SURGICAL PROBE

(71) Applicant: Verily Life Sciences LLC, Mountain View, CA (US)

(72) Inventors: Blake Eugene Hannaford, Seattle, WA (US); Eden Rephaeli, Menlo Park, CA (US); Jöelle Karine Barral, Mountain View, CA (US); Christine Denise Ching, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 381 days.

(21) Appl. No.: 14/550,560

(22) Filed: Nov. 21, 2014

(51) Int. Cl.
*A61B 18/00* (2006.01)
*A61B 18/22* (2006.01)
*A61B 19/00* (2006.01)

(52) U.S. Cl.
CPC .......... *A61B 18/22* (2013.01); *A61B 19/5212* (2013.01); *A61B 19/54* (2013.01); *A61B 2018/00577* (2013.01); *A61B 2018/00773* (2013.01); *A61B 2018/2266* (2013.01); *A61B 2018/2283* (2013.01); *A61B 2019/5441* (2013.01); *A61B 2218/007* (2013.01)

(58) Field of Classification Search
CPC ........ A61B 5/0084; A61B 2018/00636; A61B 18/20; A61B 5/22; A61B 5/54; A61B 19/5212; A61B 2018/00577; A61B 2218/007; A61B 2018/00773; A61B 2019/5441; A61B 2018/2283; A61B 2018/2266

See application file for complete search history.

(56) References Cited

U.S. PATENT DOCUMENTS 5,456,681 A * 10/1995 Hajjar .................... A61B 18/24
                                                          15/104.92
6,011,889 A *  1/2000 Daniel ................... A61B 18/24
                                                          385/115
8,535,298 B1*  9/2013 Neev .................... A61B 18/245
                                                          606/11

(Continued)

OTHER PUBLICATIONS

Matos, Leonardo S., et al., "A Novel Computerized Surgeon-Machine Interface for Robot-Assisted Laser Phonomicrosurgery," The Laryngoscope, 2013, pp. 1-8.

(Continued)

*Primary Examiner* — Scott T Luan
(74) *Attorney, Agent, or Firm* — McDonnell Boehnen Hulbert & Berghoff LLP

(57) ABSTRACT

A surgical probe is configured to be inserted into a body cavity and to emit beams of light to ablate tissue within the body cavity. The probe further includes sensors to detect properties of tissue in the body cavity and a source of suction to remove material produced by ablation of tissue within the body cavity. The sensors could be configured to operate in combination with beams of light emitted by the surgical probe to detect the location, geometry, fluorophore content, or other information about tissue in the body cavity. The surgical probe can additionally include suction port(s) to secure portions of tissue relative to the surgical probe to allow ablation of portions of the secured tissue and to allow detection of properties of portions of the secured tissue that are maintained in contact with the surgical probe by the suction port(s).

17 Claims, 10 Drawing Sheets

(56) References Cited

U.S. PATENT DOCUMENTS

| | | | |
|---|---|---|---|
| 8,568,399 B2* | 10/2013 | Azamian | A61B 17/00234 606/33 |
| 2002/0045811 A1* | 4/2002 | Kittrell | A61B 1/00096 600/407 |
| 2008/0215039 A1* | 9/2008 | Slatkine | A61B 17/205 606/9 |
| 2009/0248004 A1* | 10/2009 | Altshuler | A61B 18/18 606/33 |
| 2014/0261579 A1* | 9/2014 | Jenkins | A61B 1/123 134/166 C |

OTHER PUBLICATIONS

Bianchi, Matteo, et al., "End user interfaces and actuation systems for (micro)surgical robots: technologies and future directions," IEEE International Conference on Robots & Automation (ICRA), 2014.

Deshpande, Nikhil, et al., "Enhanced Computer-Assisted Laser Microsurgeries with a "Virtual Microscope" based surgical system," IEEE International Conference on Robots & Automation (ICRA), 2014, pp. 4194-4199.

Mattos, Leonardo S., et al. "The uRALP Project: New Technologies and Systems for Robot-Assisted Laser Phonomicrosurgery," 3rd Joint Workshop on New Technologies for Computer/Robot Assisted Surgery, 2013.

Arata, Jumpei, et al., "Neurosurgical robotic system for brain tumor removal," Int. J. CARS, 2011, 6:375-385.

Jung, Woonggyu, et al., "Miniaturized probe using 2-axis MEMS scanner for endoscopic multiphoton excitation microscopy," Proc. of SPIE, vol. 6851 (2008).

\* cited by examiner

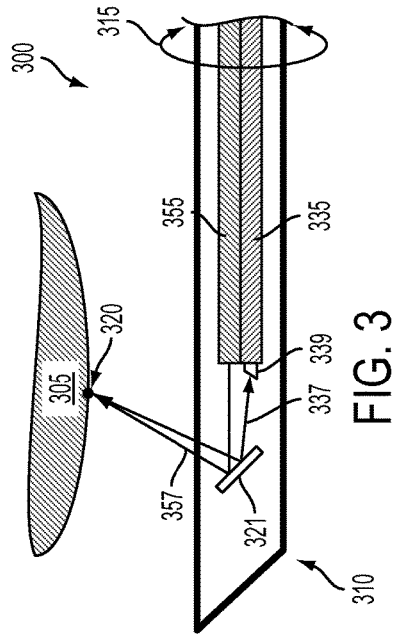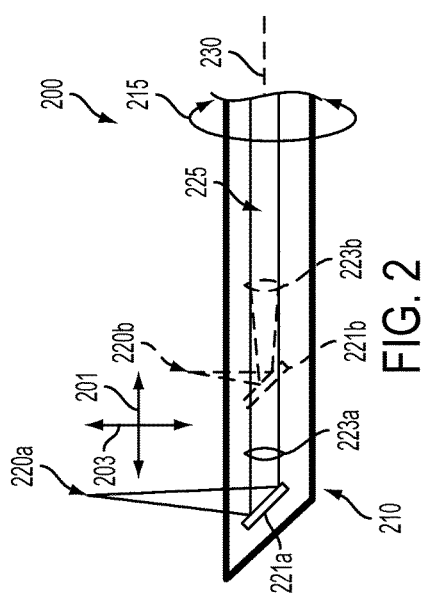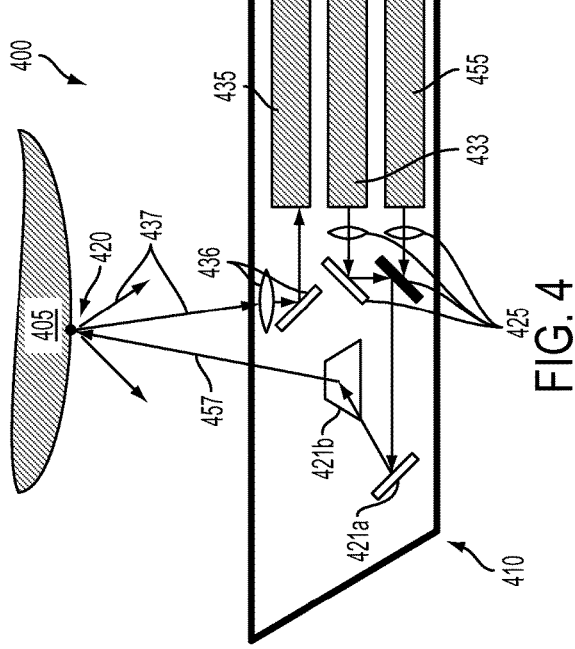

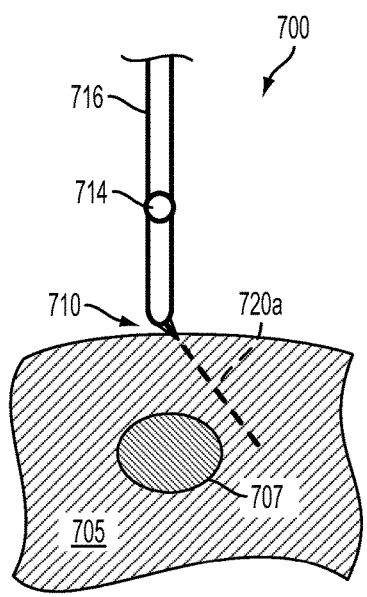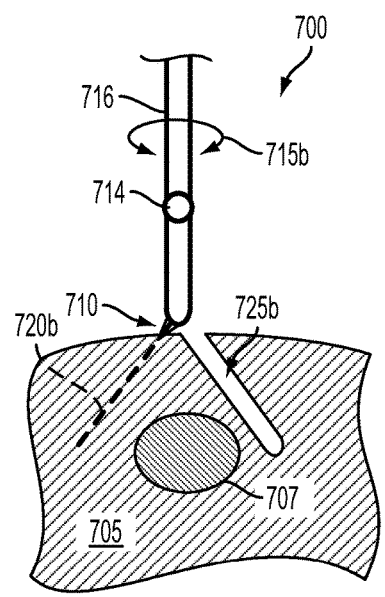
FIG. 7A　　　　　　　　　　FIG. 7B
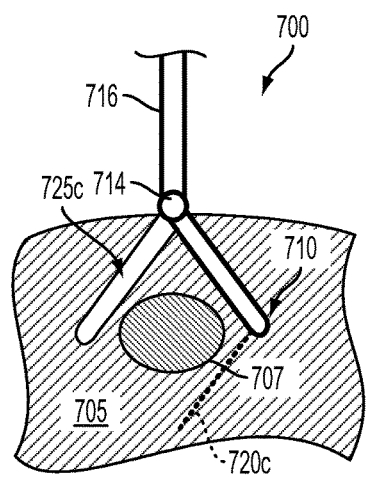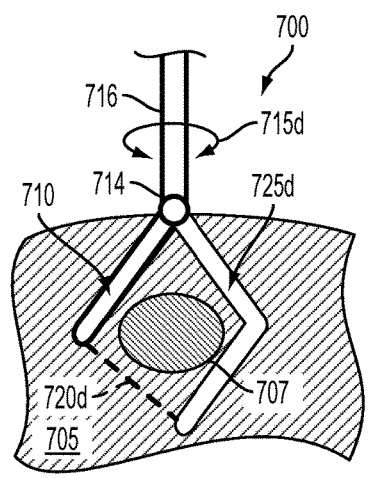
FIG. 7C　　　　　　　　　　FIG. 7D

BIOPHOTONIC SURGICAL PROBE

BACKGROUND

Unless otherwise indicated herein, the materials described in this section are not prior art to the claims in this application and are not admitted to be prior art by inclusion in this section.

A variety of laparoscopic, or otherwise endoscopic surgical systems and/or implements exist to enable surgical procedures to be performed by a surgeon operating such systems and/or implements. The surgeon could operate such systems and/or implements to perform a surgical intervention and/or to investigate a property or state of tissues of a body that are not immediately externally accessible. Such tissues could be tissues within a closed cavity of the body (e.g., within an abdominal cavity, within a thoracic cavity). Such tissues could be within an open cavity of the body or within some other cavity of the body that has some access to the outside of the body (e.g., within an esophagus, within a stomach, within a gastrointestinal tract).

SUMMARY

Some embodiments of the present disclosure provide a system comprising: (i) a surgical probe, wherein the surgical probe comprises a probe head configured to be inserted into a body cavity; (ii) a laser, wherein the laser is configured to emit a beam of illumination capable of ablating biological tissue proximate the probe head; (iii) at least one optical element, wherein the at least one optical element is optically coupled to the laser; (iv) an actuator, wherein the actuator is configured to adjust the at least one optical element; (v) a controller, wherein the controller is configured to control a location of a focus of the beam of illumination relative to the biological tissue proximate the probe head by controlling at least one of the actuator or applied suction; and (vi) at least one sensor, wherein the at least one sensor is configured to detect a property of the biological tissue proximate to the probe head.

Some embodiments of the present disclosure provide a system comprising: (i) a surgical probe, wherein the surgical probe comprises a probe head configured to be inserted into a body cavity; (ii) means for emitting laser light, wherein the means for emitting laser light are configured to emit a beam of illumination capable of ablating biological tissue proximate the probe head; (iii) at least one optical element, wherein the at least one optical element is optically coupled to the laser; (iv) actuating means, wherein the actuating means are configured to adjust the at least one optical element; (v) controlling means, wherein the controlling means are configured to control a location of a focus of the beam of illumination relative to the biological tissue proximate the probe head by controlling at least one of the actuating means or applied suction such that the location of the focus of the beam of illumination corresponds to the particular region of the biological tissue; and (vi) sensing means, wherein the sensing means are configured to detect a property of the biological tissue proximate to the probe head.

Some embodiments of the present disclosure provide a method comprising: (i) inserting a probe head of a surgical probe into a body cavity, wherein the surgical probe comprises: (a) a laser, wherein the laser is configured to emit a beam of illumination capable of ablating biological tissue proximate the probe head; (b) at least one optical element, wherein the at least one optical element is optically coupled to the laser; (c) an actuator, wherein the actuator is configured to adjust the at least one optical element; (d) a controller, wherein the controller is configured to control a location of a focus of the beam of illumination relative to the biological tissue proximate the probe head by controlling at least one of the actuator or applied suction; and (e) at least one sensor, wherein the at least one sensor is configured to detect a property of the biological tissue proximate to the probe head; (ii) operating the at least one sensor to detect a property of a particular region of the biological tissue proximate to the probe head; (iii) controlling, by the controller, the location of a focus of the beam of illumination relative to the biological tissue proximate the probe head by controlling at least one of the actuator or applied suction; and (iv) operating the laser to ablate the particular region of the biological tissue.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 2 illustrates a side cross-sectional view of an example surgical probe that is emitting a beam of light.

FIG. 3 illustrates a side cross-sectional view of an example surgical probe that is emitting a beam of light toward a portion of tissue.

FIG. 4 illustrates a side cross-sectional view of an example surgical probe that is emitting a beam of light toward a portion of tissue.

FIG. 5 illustrates a side cross-sectional view of an example surgical probe that is emitting a beam of light.

FIG. 7A illustrates a side cross-sectional view of an example surgical probe that is emitting a beam of light toward a portion of tissue containing a target tissue.

FIG. 7B illustrates a side cross-sectional view of the example surgical probe and target tissue of FIG. 7A.

FIG. 7C illustrates a side cross-sectional view of the example surgical probe and target tissue of FIG. 7A.

FIG. 7D illustrates a side cross-sectional view of the example surgical probe and target tissue of FIG. 7A.

DETAILED DESCRIPTION

Figure 1:
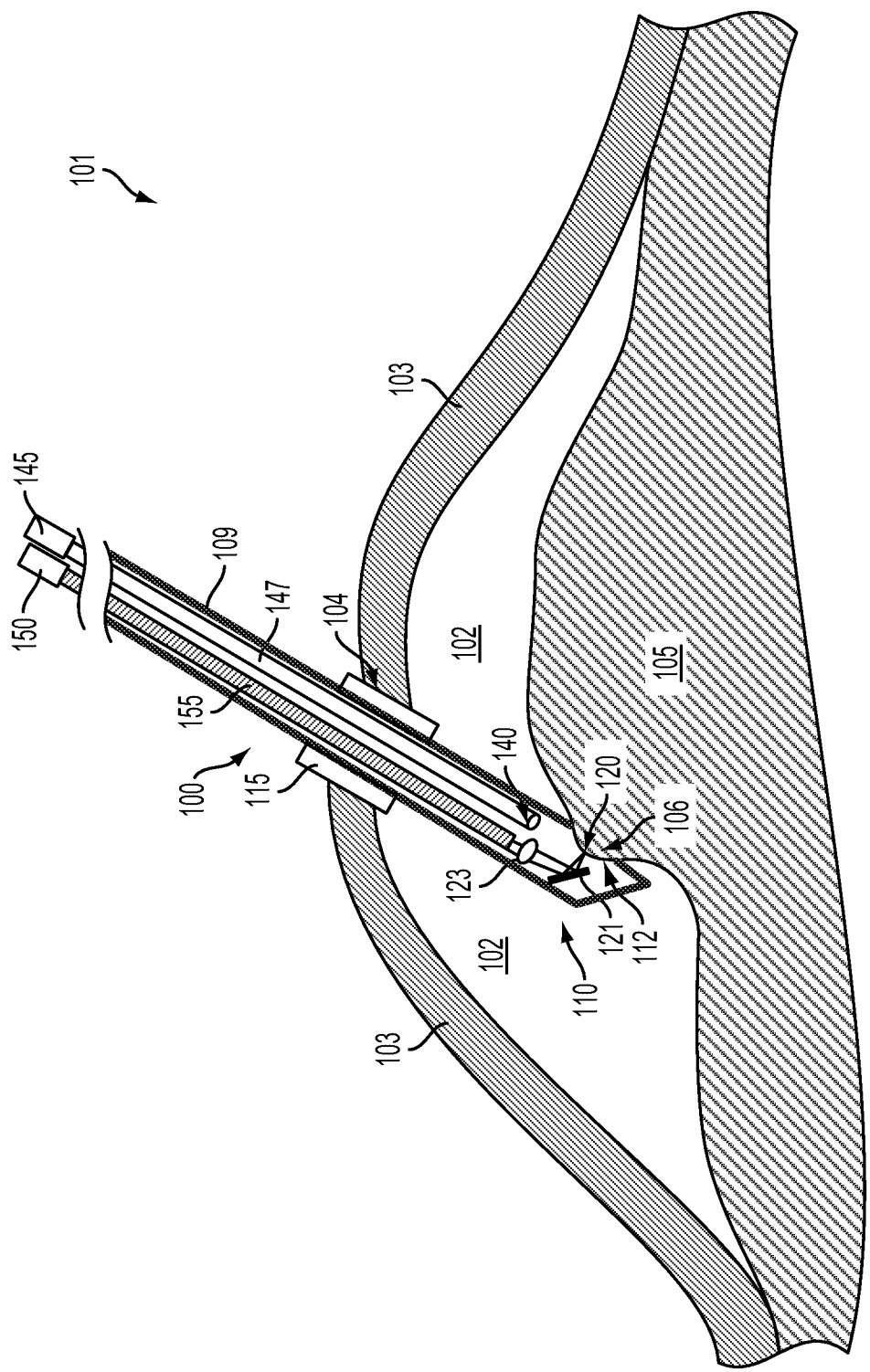
FIG. 1 illustrates a side cross-sectional view of an example surgical probe inserted into a body cavity.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body and/or tissues thereof, it is contemplated that the disclosed methods, systems and devices may be used in any environment where spectrographic imaging and/or identification of tissues or other objects or elements of an environment is desired. The environment may be any living or non-living body or a portion thereof, a work piece, an implantable device, etc. Moreover, while the present disclosure describes embodiments for use in vivo, one of skill in the art will also recognize that in vitro applications are possible as well. Accordingly, the environment may also include a test tube or other vessel for holding a fluid, a transplant tissue, and/or a stereotaxically or otherwise immobilized tissue.

I. OVERVIEW

A surgical probe and/or elements thereof can be configured to be inserted into a body cavity to allow a variety of surgical or other applications of the surgical probe. The surgical probe could include a variety of sensors configured to detect properties of biological tissue within and/or proximate to the body cavity. The surgical probe could include a variety of surgical tools or other elements configured to alter, ablate, ligate, tag, mark, incise, biopsy, suture, manipulate, or otherwise interact with biological tissue within and/or proximate to the body cavity. These applications could include controlling the location of the surgical probe and/or elements thereof relative to the body cavity and/or controlling the location and/or direction of one or more beams of light (e.g., the location of a focus of a beam of light emitted by a surgical tissue-ablating laser) relative to the body cavity and/or other elements of the surgical probe. The surgical probe could include a probe head from which such beams of light could be emitted and/or that could contain one or more sensors. Further, such a probe head could include collection ports or other elements configured to allow ablated material or other gases or fluids within the body cavity to be removed from the body cavity, e.g., by application of suction through a collection port.

One or more beams of laser light (or other beams of illumination) could be emitted from a probe head of a surgical probe to allow for ablation of biological tissue within a body cavity and/or according to some other application. The direction of such beams, the distance between the probe head and a focus of such beams, the location of a focus of such emitted beams relative to the probe head and/or elements of the body cavity, the power of such beams, or some other properties of beams of illumination emitted by a probe head could be controlled. For example, the location of focus and power of an emitted beam of illumination could be controlled to ablate a target tissue in the body cavity having a location corresponding to the controlled location of focus of the beam. A laser or other light-emitting element configured to produce illumination that forms such beams could be located within the surgical probe (e.g., within a tubular housing of the surgical probe that is partially inserted into the body cavity). Additionally or alternatively, such a laser or other light-emitting element could be disposed in some other location and optically coupled to optics (e.g., an actuated mirror) of the probe head or other elements of the surgical probe via an optical fiber or some other means.

The direction, location of focus, or other properties of a beam of illumination emitted by a surgical probe could be controlled in a variety of ways. In some examples, the surgical probe could include one or more optical elements configured to reflect, refract, diffract, polarize, focus, or otherwise control one or more properties of the beam of illumination. For example, the surgical probe could include a mirror and an actuator configured to adjust, affect, or otherwise control a location and/or angle of the mirror such that the location and/or angle of the beam of illumination relative to the surgical probe (e.g., relative to the probe head of the surgical probe) and/or relative to biological tissue proximate the probe head could be controlled. Additionally or alternatively, the location and/or orientation of elements of the surgical probe (e.g., the probe head) containing such optics could be controlled to allow the properties of the beam of illumination to be controlled.

Ablation of biological tissue by beams of illumination can include providing, via the beam of illumination, sufficient power to a region of biological tissue that one or more irreversible processes occur in the biological tissue. These processes could include vaporization, coagulation, or other heat-related processes involving water, proteins, or other contents of the biological tissue. Ablation of the biological tissue can result in the production of vapor (e.g., water vapor), particulates (e.g., particles of tissue propelled away from the site of the ablation), and/or smoke (e.g., condensates or other particulates suspended in air or other gas within the body cavity) within the body cavity. Such results of tissue ablation could interfere with the operation of the surgical probe, for example, by occluding biological tissue from view of optical sensors of the surgical probe and/or by preventing beams of illumination emitted by the surgical probe from being transmitted to biological tissue (e.g., by preventing sufficient emitted energy from being received by a specified portion of biological tissue to ablate the tissue).

Smoke or other material resulting from ablation could be removed from the body cavity by suction applied via a collection port of the surgical probe. Additionally or alternatively, beams of illumination could be emitted from the surgical probe via a window or other optical element, and the surgical probe could include means for clearing particulates or other fouling matter from the window or other optical element. This could include rinsing the particulates off of the surgical probe (e.g., by applying a saline solution or other rinsing fluid), absorbing and/or suctioning fluids from the surgical probe (e.g., by application of an absorbent material), by scraping or wiping the surgical probe (e.g., using a scraper, wiper, or other actuated element of the surgical probe), or some other method of clearing fluids, particulates, or other debris from one or more regions (e.g., windows or other optical elements) of the surgical probe.

The surgical probe could include a variety of sensors configured to detect one or more properties of biological tissue proximate to the surgical probe in a body cavity. Such sensors could be configured to detect the presence, location, temperature, pH, color, electrical impedance, electrical impedance spectrum, emission spectrum, excitation spectrum, absorbance spectrum, reflectance spectrum, refractive index, compliance, stiffness, or some other electrical, optical, mechanical, magnetic, chemical, topographical, or other information about one or more portions of tissue proximate the surgical probe. Such sensors could be configured to detect information about tissue without directly contacting the tissue, e.g., by generating and/or receiving electrical, magnetic, or electromagnetic fields, visible light, infrared radiation, ultraviolet radiation, or some other transmitted and/or directed energies between the tissue and the surgical probe.

Additionally or alternatively, such sensors could be configured to detect information about tissue through direct contact with one or more points of the tissue, e.g., by detecting electrical (e.g., an impedance, and impedance spectrum, an electrochemical potential), thermal (e.g., temperature, heat conductance, specific heat), mechanical (e.g., stiffness), and/or chemical (e.g., pH, the concentration of one or more analytes) properties of the tissue through direct contact between the tissue and one or more electrodes, probes, or other sensing elements. Further, detection of properties of tissue by sensors of the surgical probe could be facilitated by markers, contrast agents, nanoparticles, nanosensors, or other elements introduced into the tissue (e.g., by the introduction of a fluorophore configured to selectively interact with an analyte of interest in the tissue).

In some examples, sensors of the surgical probe could be configured to detect properties of the tissue by illuminating the tissue and detected light emitted from the tissue in response to the illumination. For example, the surgical probe could include light emitters, mirrors, lenses, or other elements configured to illuminate a particular region of tissue at a specified location and/or in a specified direction relative to a probe head of the surgical probe and to detect light responsively emitted from the illuminated region of tissue. This could include illuminating the region of tissue using the light source and/or optical element(s) that are also configured to emit beams of light to ablate biological tissue. Additionally or alternatively, a separate light source and/or separate optical element(s) could be used to illuminate particular regions of tissue to detect properties of the particular regions of tissue.

The light emitted from the illuminated region of tissue could be detected with a camera or other light-sensitive element(s), and the location of the region of tissue relative to the probe head could be determined (e.g., through triangulation). A variety of wavelengths of light could be used to illuminate the region of tissue and/or light responsively emitted from the tissue could be detected at a variety of wavelengths to enable the detection and/or determination of spectrographic information about the region of tissue (e.g., a excitation wavelength, an emission spectrum, an absorption spectrum, a reflectance spectrum, or some other spectrographic information). Additionally or alternatively, the presence and/or one or more properties (e.g., a state of binding to a particular analyte) of one or more fluorophores in the region of tissue could be detected (e.g., by illuminating the region of tissue with light at an excitation wavelength of the fluorophore and detecting light responsively emitted from the fluorophore at an emission wavelength of the fluorophore).

A light source of the surgical probe could emit light at a single wavelength (or light having some other properties that are substantially the same over time) or could emit light at a plurality of wavelengths during a plurality of different periods of time to illuminate portion of biological tissue. Further, at least one sensor could detect light responsively emitted from the biological tissue within a single narrow range of wavelengths, within a wide range of wavelengths, and/or within a plurality of ranges of wavelengths.

In some examples, the surgical probe could include a further light source configured to illuminate one or more portions of the biological tissue proximate the surgical probe with a further beam of illumination at any of a plurality of respective different wavelengths. Such a light source could be optically coupled to at least one optical element in common with an ablation laser such that a location of a focus of the further beam of illumination is substantially the same as the location of a focus of a beam of illumination emitted by the ablation laser. At least one sensor of the surgical probe (e.g., a light sensor, a camera, a spectrometer) could then be operated to receive light emitted from the biological tissue in response to illumination by the further beam of illumination, and spectrographic content of the received light could then be determined.

The further light source could include a tunable laser controllable to emit light at any of a plurality of different wavelengths (e.g., wavelengths ranging between approximately 400 nanometers and approximately 2.5 micrometers). Such a tunable laser could include an excimer laser, a dye laser, a $CO_2$ laser, a free-electron laser, or some other laser element configured to emit light at a plurality of different, controllable wavelengths. In some examples, the wavelength of the light emitted by such a tunable laser could be controlled by controlling a geometry or size of one or more elements (e.g., a reflector, a resonating cavity) of the tunable laser. In some examples, a Bragg reflector or other element of the tunable laser could be rotated or otherwise actuated to control the wavelength of light emitted by the tunable laser. In some embodiments, the further light source could include a plurality of lasers configured to emit light at wavelengths corresponding to respective different wavelengths, and operation of the further light source to emit light of a particular wavelength could include operating the corresponding laser of the further light source to emit light at the controlled wavelength. Other configurations and operations of a tunable laser and/or a further light source of the surgical probe are anticipated.

Spectrographic information about a biological tissue, surgical instrument, foreign body, or other portion of a surgical environment could be detected and/or determined by illuminating the portion of the biological tissue, detecting light that is emitted from the portion in response to the illumination, and determining some spectrographic content of the received light. Determining spectrographic content could include generating a spectrum (e.g., a reflectance spectrum, an emission spectrum, an absorbance spectrum) from the received light by detecting a plurality of amplitudes of the received light within a respective plurality of ranges of wavelengths. That is, the spectrographic content could include a plurality of detected and/or determined amplitudes corresponding to wavelengths of the received light, e.g., at specified wavelengths linearly spaced within a range of wavelengths. Such a determined spectrographic content could be generated related to the illumination of the contents by light of a single wavelength. Alternatively, such spectrographic content could be determined a plurality of times corresponding to illumination of the contents during a respective plurality of different periods of time by light of a respective plurality of different single wavelengths.

Spectrographic contents could include a description of one or more features of a spectrum or other wavelength-dependent optical properties of the contents; for example, spectrographic content could include an absolute or relative amplitude, mean wavelength, width at half maximum, or other descriptive information about a peak or other feature of a spectrum of a portion of a surgical environment. Such spectrographic contents could be determined based on a determined and/or detected spectrum (e.g., by extracting an amplitude, width, or wavelength location of a peak within a determined and/or detected plurality of detected amplitudes corresponding to wavelengths of light received from the surgical environment). Alternatively, such spectrographic contents could be determined in other ways, e.g., through an iterative process that includes controlling a wavelength of light illuminating a portion of the surgical environment to minimize an amplitude of light received from the portion in response to the illumination, e.g., to determine a wavelength of a peak within the absorbance spectrum of the portion. Other types of spectrographic contents and methods of detecting and/or determining such spectrographic contents are anticipated.

Ablation of a particular region of biological tissue and/or detection of one or more properties of the region of biological tissue could be improved and/or facilitated by securing the location of the region of tissue relative to elements (e.g., to a probe head) of the surgical probe. This could include applying securing forces to regions of tissue via a variety of methods. Tissue could be secured relative to a probe head of the surgical probe by adhesives, clamps, hooks, sutures, magnetic fields (in examples wherein a magnetic material is present in and/or has been introduced into the region of tissue), suction, or some other means. For example, the probe head of the surgical probe could include a tissue entrance port through which suction could be applied to a portion of tissue to secure the portion of tissue relative to the tissue entrance port and/or other elements of the surgical probe.

The surgical probe could be configured to emit an ablating beam of illumination to locations proximate to the tissue entrance port such that specified regions of a secured portion of tissue could be ablated. Additionally or alternatively, one or more sensors of the surgical probe could be configured to detect one or more properties of tissue when the tissue is secured by suction applied via the tissue entrance port. For example, one or more sensing elements (e.g., electrodes) configured to detect properties of biological tissue through direct contact could be disposed relative to the tissue entrance port such that the sensing elements are maintained in direct contact with regions of a portion of tissue when the portion of tissue is secured by suction applied through the tissue entrance port. Other applications of the surgical probe could be facilitated by the surgical probe being configured to secure tissue, e.g., the surgical probe could be configured to displace, retract, dissect, or otherwise manipulate secured tissues and/or biological tissue attached to such secured tissues.

Other configurations, modes and methods of operation, and other embodiments are anticipated. Systems and methods described herein could include additional imaging modalities to improve the identification of the contents of portions of a surgical environment according to an application. A system as described herein could include multiple light emitters, multiple optical elements and/or illumination-steering actuated optical systems, multiple sensors, multiple tissue entrance ports, multiple collection ports, and/or additional components according to an application. The system could be applied toward implementing, planning, and/or assessing a surgical intervention (e.g., ablation of a tissue), imaging a tissue, or some other application. Further, systems as described herein could be applied to the manipulation and/or identification of the contents of portions of environments other than surgical environments (e.g., food processing environments, industrial fabrication environments, environments under study in scientific research) by ablating, detecting properties of, securing (e.g., via suction), or other interactions with or manipulations of portions of the other environments. Other applications and configurations of systems as described herein are anticipated.

It should be understood that the above embodiments, and other embodiments described herein, are provided for explanatory purposes, and are not intended to be limiting.

Further, the term "surgical intervention" as used herein should be understood broadly to include any activities applied toward the modification of the anatomy and/or tissue(s) of a human or animal body by the application of external forces and/or energies to the human or animal body; e.g., incision, ablation and/or cauterization by RF or other directed energies, excision, resection, suturing, application of surgical adhesives, stapling, transplanting, cauterizing, sawing, abrading, applying a surgical fluid to (e.g., sterile, isotonic saline), cooling, heating, or any other surgical operation or procedure.

II. EXAMPLE SURGICAL ENVIRONMENT

FIG. 1 illustrates an example surgical environment 101. The surgical environment 101 includes biological tissue (e.g., 103, 105, 106, 120) that is subject to a surgical intervention using a surgical probe 100. The biological tissue includes a deep tissue 105 located beneath overlying tissue 103 (e.g., skin). The overlying tissue 103 includes an incision 104 through which the surgical probe 100 has been inserted (via a trocar 115 installed in the incision 104) into a body cavity 102 that exists between the overlying tissue 103 and the deep tissue 105. The deep tissue 105 includes a secured portion of tissue 106 that is being secured by the surgical probe 100. The deep tissue 105 additionally includes a particular region of tissue 120 that is being illuminated by illumination from the surgical probe. Note that the illustration of tissue, surgical probes, surgical instruments, and/or foreign bodies in FIG. 1 and elsewhere herein are intended as non-limiting illustrative examples. Systems and methods described herein could be applied to a variety of organs, tissues, and tissue types, e.g., muscle tissue, skin tissue, liver tissue, kidney tissue, connective tissue, pancreatic tissue, bowel tissue, prostate tissue, cortical tissue, nerve tissue, lung tissue, or some other type or types of tissue at some other location(s) of a body. Further, a surgical probe could be inserted into a body cavity through a natural opening in the body cavity (e.g., the surgical probe could be inserted into a gastrointestinal body cavity via the mouth) rather than through an incision made into the body cavity through an overlying tissue. Note that the surgical probe could additionally be operated to ablate, detect, manipulate, or otherwise interact with surface tissues (e.g., skin, external mucosa) of a body, as well.

Surgical probe 100 includes a generally tubular housing 109 that is configured to be inserted into the body cavity such that the location of a probe head 110 (i.e., a housing, assembly, or other element(s) located at the end of the surgical probe) relative to biological tissue (e.g., 105) within the body cavity 102 can be controlled. The surgical probe 100 includes a tissue entrance port 112 through which suction can be applied to secure the portion of tissue 120 relative to the probe head. The surgical probe 100 additionally includes a light source 150 (e.g., a laser) configured to emit illumination capable of ablating biological tissue. The light source 150 is optically coupled, via an optical fiber 155, to a mirror 121 and lens 123 such that the beam of illumination is emitted toward a particular region of tissue 120 of the deep tissue 105 in the body cavity 102. The surgical probe additionally includes a collection port 140 coupled via a collection tube 147 to a suction source 145 that is configured to collect material produced by ablation of biological tissue (e.g., smoke, fluids, particulates) by beams of illumination emitted by the surgical probe 100.

The probe head 110 is configured to be inserted into the body cavity 102 via a trocar 115 installed in the incision 104 into the body cavity 102. Such a trocar could be configured and/or formed according to a standard such that alternative surgical tools could be inserted into the body cavity via the trocar 115. The trocar could be configured to provide an inflating gas (e.g., carbon dioxide) to create the body cavity once the trocar is installed 115, to increase and/or decrease the size of the body cavity, to maintain the size of the body cavity 102, or according to some other application. Further, the surgical probe 100 could be inserted through more than one incision and/or trocar through more than one tissue and/or more than one layer of tissue (e.g., through skin, muscle, and peritoneum to access deep tissue within the abdominal cavity). Additionally or alternatively, the probe head 110 could be configured to be installed into a body cavity (e.g., 102) without such a trocar. For example, the surgical probe 100 could be configured and/or operated to be inserted into a body cavity through a natural opening of the body cavity (e.g., into a stomach or other gastrointestinal cavity via the mouth, into the trachea or lungs via the mouth, into a nasal sinus via the nose). Additionally or alternatively, the probe head 110 could be disposed proximate to a surface tissue (e.g., skin) and the surgical probe 100 could be operated to detect, ablate, or otherwise interact with the surface tissue.

The deep tissue 105 could include any tissues or organs of interest in a surgical or medical context. For example, the deep tissue 105 could be tissue suspected and/or known to have and/or to be causing an adverse health state of a patient (e.g., tissue containing a tumor, an abnormal portion of vasculature, an adhesion, an occlusion, a stenosis, an infection, etc.). The surgical probe 100 could be operated to detect information about such a subject tissue, for example, to diagnose the presence, type, or other information about a growth or tumor of the subject tissue. The surgical probe could additionally or alternatively be operated to ablate such a tumor or growth, to ablate some other tissue according to an application, or to otherwise interact with and/or manipulate biological tissue. Further, the surgical probe could be configured to allow other applications, for example, electrocautery (using electrodes disposed on the surgical probe), biopsy, organ or tissue removal, local delivery of drugs or other substances to biological tissue, suturing, stapling, or other surgical or diagnostic applications.

Biological tissue in the body cavity 102 could have a variety of properties related to a health state of a patient and/or of the biological tissue. For example, an absorption, emission, or other spectrum, an electrical impedance, a specific heat, an electrical impedance spectrum, or some other property of a biological tissue could be related to the presence of water, melanin, hemoglobin, cancer cells, infectious microorganisms, or other substances in the tissue. In another example, an excitation and/or emission spectrum of a biological tissue could be related to the presence of one or more fluorophores, chromophores, or other fluorescent elements on or within in the biological tissue. Properties of a biological tissue (e.g., absorption spectrum, excitation spectrum, emission spectrum, electrical impedance spectrum) could be related to a medical state of the biological tissue. For example, a cancerous tissue could have an absorbance spectrum (e.g., could be a different color) different from the absorbance spectrum of a non-cancerous tissue. Additionally or alternatively, a fluorophore, chromophore, or other marking agent could be introduced (e.g., by direct application, by injection into the bloodstream of a patient) to a particular tissue (e.g., a cancerous tissue) and one or more spectrographic or other properties of the marking agent and/or of the combination of the marking agent and the particular tissue could be detected to determine the location, shape, or other properties of the particular tissue. Such a marking agent could be configured to selectively interact with a particular tissue (e.g., by binding to a protein or other element specific to the particular tissue) such that systemic application of the marking agent (e.g., by injection into the bloodstream of a patient) could allow the marking agent to be concentrated in the particular tissue. In another example, the absorption spectrum of a tissue could be related to the amount of oxygenation of hemoglobin in the tissue, such that the oxygen content, perfusion rate, or other information about the tissue could be determined based on a determined and/or detected absorption spectrum or features thereof.

The surgical probe 100 includes a mirror 121 and lens 123 that are adjusted, affected, or otherwise actuated by one or more actuators (not shown) to control the location, relative to the probe head 110 and/or relative to biological tissue proximate the probe head, of a focus of a beam of illumination emitted by the surgical probe 100. As shown in FIG. 1, the focus of the beam of illumination is being controlled to intersect with the particular region of tissue 120 such that the particular region of tissue 120 can be ablated. An angle, location, or other properties of the mirror 121 and/or lens 123 could be adjusted, affected, or otherwise controlled (e.g., by one or more electromechanical or other actuators) to control the location of the focus of the beam of light and/or the angle of the beam of light relative to the probe head 110 and/or relative to biological tissue proximate the probe head. Further, the surgical probe could include additional optical elements, having additional respective actuated properties (e.g., locations, angles) configured to control the location of a focus of the beam of light relative to the probe head 110 and/or relative to other elements of the surgical probe 100 and/or biological tissue (e.g., 103, 105, 106).

As shown in FIG. 1, light emitted by the light source 150 is coupled to optical elements (e.g., 121, 123) of the surgical probe 100 via an optical fiber 155. This is intended as a non-limiting example; illumination emitted by the light source 150 could be coupled to optical elements of the surgical probe 100 by a variety or means, including but not limited to one or more optical fibers, relay lenses and/or relay lens systems, mirrors, diffraction gratings, lenses, or other optical elements. Further, more than one light source could produce one or more beams of illumination that could be delivered to biological tissue via optical elements of the surgical probe 100. For example, two or more light sources could produce respective beams of light that could be combined and coupled to optical elements of the surgical probe 100 to enable applications of the surgical probe 100 (e.g., a first light source could be configured to emit a beam of illumination capable of ablating biological tissue, while a second light source could be configured to emit a beam of illumination capable of exciting a fluorophore in the tissue, e.g., to enable imaging of the fluorophore in the tissue). Further, the light source 150 could be disposed within the tubular housing 109 or other elements of the surgical probe 100, proximate to the probe head 110, or at some other location according to an embodiment.

The collection port 140 is configured to collect smoke or other material produced by ablation of biological tissue by beams of illumination emitted by the surgical probe 100. This could include providing suction continuously, providing suction during and/or after operation of the surgical probe 100 to ablate tissue, providing suction in response to detection of an amount of produced smoke of other material produced by ablation proximate to the probe head 110, providing suction in response to a detection and/or determination that the operation of the surgical probe 100 is being degraded by the presence of materials produced by ablation of biological tissue (e.g., beam energy is being absorbed by ablated material and/or an emitted beam is being de-focused by ablated material), or providing suction according to some other consideration or factor. Further, such collection of ablated material could be performed by providing suction through a number of collection ports and/or by providing negative suction (i.e., by forcing air or other gases out of) via one or more ports. Additionally or alternatively, rinsing fluids, scraping means, absorbing means, or other elements could be provided as part of the surgical probe 100 to remove materials produced by ablation of biological materials by the surgical probe 100.

The surgical probe 100 includes a tissue entrance port 112 through which suction can be applied to secure the portion of biological tissue 120 relative to the probe head 110. Such suction could be provided by a suction source (not shown) in addition to and/or a part of the suction source 145 configured to provide suction via the collection port 140. Additionally or alternatively, the surgical probe 100 could be configured to provide suction via the collection port 140 and further via the tissue entrance port 112 to collect ablation material and to secure the portion of tissue 120 relative to the probe head 110, respectively. This could include operating the surgical probe 100 during alternating periods of time to alternatively provide suction through the tissue entrance port 112 to secure tissue (e.g., to secure tissue during operation of the surgical probe 100 to ablate part of the secured portion of tissue) and to collect ablated materials (e.g., after part of the secured portion of tissue has been ablated and the portion of tissue is no longer secured in the tissue entrance port 112). Additionally or alternatively, a passive aperture, active valves, or other elements of the surgical probe 100 could be configured and/or operated such that suction can be provided by the suction source 145 via the collection port 140 to collect ablated materials (e.g., to provide a specified volume flow rate through the collection port 140) and such that suction can be provided by the suction source 145 via the tissue entrance port 112 such that the portion of tissue 106 is secured (e.g., by providing a specified pressure within the tissue entrance port 112 relative to a pressure outside of the probe head 110).

The surgical probe 100 can additionally include one or more sensors (not shown). Such sensors could be non-contact sensors (e.g., optical sensors, electrical and/or magnetic field sensors, acoustical sensors, or some other sensors configured to interact with tissue via some separation) and/or contact sensors (e.g., electrodes, electrical impedance sensors, electrochemical electrodes, pH sensors, temperature sensors, mechanical stiffness sensors). Such sensors could be a part of and/or operate in concert with other elements of the surgical probe 100. For example, a camera or other optical sensor could be configured to detect one or more properties of biological tissue by receiving light emitted from the biological tissue in response to illumination by the beam of illumination emitted by the light source 150 and/or by light emitted from some other source and delivered to the biological tissue via the optical fiber 155, lens 123, mirror 121, and/or some other optical element(s) of the surgical probe 100. In another example, a mechanical property of biological tissue (e.g., a stiffness) could be detected by detecting a property of the tissue when secured by suction provided via the tissue entrance port 112 (e.g., by detecting a relationship between a level of suction applied and a degree of dimpling of the tissue through the tissue entrance port 112). Other sensors and/or properties thereof could be detected by the surgical probe 100. In some examples, one or more sensors of the surgical probe 100 could have a limited field of view (e.g., could be capable of detecting a property of tissue within a specified volume and/or in a specified direction relative to the probe head) and a location, angle, and/or orientation of the probe head 110 could be controlled (e.g., scanned) to allow detection of properties of biological tissue at a variety of locations within the body cavity 102. Additional configurations and operations of the surgical probe 100 to detect properties of tissue within a body cavity are anticipated.

The location, angle, and/or orientation of the probe head 110 could be controlled to allow ablation, detection, displacement, dissection, or other manipulations of biological tissue at a variety of locations within the body cavity 102. This could include a surgeon operating a grip or other means of the surgical probe 100 to control the location and/or orientation of the surgical probe 100. Additionally or alternatively, an armature or other means of securing and/or actuating the location and/or orientation of the surgical probe 100 relative to tissue of a patient could be operated by a surgeon and/or by an automated surgical system to control the location, angle, and/or orientation of the probe head 110 relative to one or more target biological tissues. Such operation could be performed relative to scans or other information about the biological tissues. For example, the location of a tumor could be determined based on an MR, CT, or other scan image of the tissue, and the surgical probe 100 and/or elements thereof (e.g., probe head 110) could be positioned based on such information. Such operation could allow the surgical probe 100 to ablate biological tissue, detect properties of biological tissue, or otherwise interact with biological tissue across a broad area and/or volume within the body cavity. Further, the surgical probe 100 could have one or more articulations and/or or could include one or more actuated flexible portions such that an overall shape of the surgical probe 100 could be controlled to control the location, angle, and/or orientation of the probe head 110, to allow the surgical probe 100 to access body cavities via curved or otherwise non-straight-line incisions or other means of cavity access (e.g., via an esophagus, trachea, or other curved region or structures.

The illustrated surgical probe 100 or other embodiments illustrated herein could be included and/or operated as part of an automated and/or semi-automated robotic surgical system. For example, the surgical probe 100 could be disposed as a laparoscopic tool of a multi-arm robotic surgical system. Other arms of such a surgical system could provide suction, cutting implements, tissue and/or tool securing implements (e.g., hemostats, forceps, needle holders), or other surgical tools that could be operated independently and/or in concert with the operation of the surgical probe 100. Further, information about biological tissue in a body cavity detected using elements of the surgical probe 100 could be made available to such a robotic surgical system.

Information about a portion biological tissue in a body cavity or other surgical environment (e.g., the identification of a portion of biological tissue as containing a tumor, a fluorophore, or some other target, the determination of a tissue type of or other information about such a portion of biological tissue, the determination of a location and/or shape of a portion of biological tissue relative to the probe head 110) could be determined using the surgical probe 100. For example, such determined information could be displayed to a surgeon, pathologist, or other person to inform some course of action; e.g., to inform a surgical intervention (e.g., to indicate the location and extent of a diseased tissue to be incised, resected, ablated, or otherwise modified), to inform a course of treatment, or to perform some other action. Additionally or alternatively, such information could be used to implement a surgical intervention by a robotic surgical system.

Automated surgical interventions (e.g., surgical interventions performed wholly or partially under the control of an artificial system) could involve engaging in an interaction with a target tissue (e.g., ablating a tissue containing cancer cells) while avoiding interaction with other biological tissue and/or non-biological contents of a surgical environment. In some examples, the surgical environment could include blood vessels, nerves, tendons, or other sensitive tissues and performance of a surgical intervention (e.g., ablation) on such tissues could cause a negative outcome (e.g., blood loss, tissue necrosis, muscle paralysis, loss of sensation). The surgical probe 100 could include sensors or other elements configured to detect the presence, location, or other information about such tissues and could be configured to operate relative to such information such that such tissues are not ablated or otherwise damaged.

III. CONTROL OF TISSUE ABLATION BY A SURGICAL SYSTEM

A surgical probe as described herein can include at least one light source (e.g., a laser) configured to generate a beam of illumination that can, via interaction with one or more optical elements (e.g., mirrors, lenses) of the surgical probe, ablate biological tissue at a controlled location relative to the surgical probe (e.g., relative to a probe head or other housing or component of the surgical probe). Additionally or alternatively, elements of the surgical probe containing such optical elements (e.g., a probe head containing one or more actuated optical elements) could be translated and/or rotated to control the location of biological tissue ablated by beam of illumination emitted from the surgical probe.

The controlled location can be a location of a focus of the emitted beam of illumination relative to elements of the surgical probe (e.g., relative to a probe head), and can be controlled by the operation of one or more actuators of the surgical probe configured to control one or more optical elements of the surgical probe and/or to control the location and/or orientation of elements of the surgical probe. The surgical probe could be configured and/or operated to illuminate a particular region of biological tissue at a time (e.g., by emitting a beam to illuminate a particular region comprising a spot, a line, or some other shape of tissue) and scanning across a portion of biological tissue to illuminate a plurality of portions over time.

In examples, the surgical probe additionally includes one or more sensors configured to detect one or more properties of biological tissue, e.g., of biological tissue at the controlled location of the focus of the beam of illumination emitted by the surgical probe. The operation of the surgical probe (e.g., to ablate biological tissue at a particular location) could be based on properties of biological tissue as detected using the surgical probe. For example, the surgical probe could be operated to detect the presence of cancer cells in a particular region of biological tissue (e.g., by detecting the presence of a fluorophore in the tissue that is configured to selectively interact with cancer cells), and to ablate regions of tissue found to contain cancer cells. The surgical probe could include further elements and/or be configured to provide additional functionality. In some examples, the surgical probe could include means for suctioning, wiping, absorbing, or otherwise removing or relocating materials created by the operation of the surgical probe to ablate biological tissue. In some examples, the surgical probe could include forceps, suction ports, adhesives, hooks, or other means configured to secure portions of biological tissue for a variety of applications.

Actuators of a surgical probe could be configured in a variety of ways to control the location of the focus of beams of light emitted by the surgical probe by, for example, controlling the location, orientation, or other properties of one or more optical elements of the surgical probe. Additionally or alternatively, such actuators could act to control a location, orientation, or other properties of the surgical probe and/or of housings or subcomponents thereof. For example, the surgical probe could include a probe head configured to be inserted in a body cavity and from which the beam of illumination is emitted, and the actuators could be configured to control the location, angle, orientation, or other properties of the probe head and/or of optical elements disposed within the probe head. Actuators could include linear actuators (i.e., actuators configured to control the location of an actuated element in a specified direction), rotational actuators (i.e., actuators configured to control an absolute or relative angle of one or more elements of the surgical probe), or some other actuators. In some examples, an actuator could be configured to control a property (e.g., a location, an angle, an orientation, an optical power, a degree of curvature of a mirror or lens) of an element of the surgical probe via one or more transduction means, for example, one or more gears, levers, screws, pumps, or other elements.

Actuators could include electromechanical motors, galvanometers, solenoids, or other elements configured to control one or more elements of the surgical probe by producing a magnetic field. Additionally or alternatively, actuators could include electrostatic elements, piezoelectric elements, electrowetting elements, bimetallic or other thermally-deformable elements, shape-memory alloy elements, or some other elements. Further, actuators could include hydraulic, pneumatic, or otherwise fluid-controlled elements. Actuators could be specified to fit within an element of the surgical probe (e.g., within a probe head, a tube, or other element(s)), to have a specified rotational, angular, linear, or other bandwidth, absolute and/or relative repeatability, accuracy, resolution, or other properties relative to an application of the surgical probe. Such specified properties could be specified relative to a mass, friction, stiction, or other properties of optical and/or other elements of the surgical probe actuated by the actuators.

Further, actuators of the surgical probe could be located proximate to or distant from actuated elements (e.g., mirrors, lenses, probe head(s)) of the surgical probe. That is, actuators could be disposed within a probe head or otherwise at the end and/or within a tube or other element of the surgical probe that is configured to be inserted into a body cavity. Alternatively, actuators could be disposed further from actuated elements and mechanically, hydraulically, pneumatically, or otherwise coupled to the actuated element(s) that may be disposed within a probe head or otherwise at the end and/or within a tube or other element of the surgical probe. For example, a pneumatic source (i.e., an actuator configured to control a pressure, flow rate, or other properties of air or other gases within a pneumatic line, cylinder, piston, or other pneumatic element) could be disposed outside of a body cavity into which a probe head of the surgical probe has been inserted. The pneumatic source could be coupled (e.g., via pneumatic tubes or hoses) to pistons, cylinders, or other pneumatic elements disposed within the probe head and configured to transduce pneumatic energy (e.g., pressures, gas flows) from the pneumatic source into a translation, rotation, or control of a property of an optical element or other component of the surgical probe. Cables, rods, gears, screws, hoses, pipes, or other elements could be configured to couple actuators of a surgical probe to actuated elements (e.g., one or more optical elements) of the surgical probe. Further, such actuator coupling elements (e.g., cables, rods, screws) could be configured to operate across, through, and/or around hinges, bearings, flexures, or other actuated or otherwise flexible elements of a surgical probe such that actuated elements of the surgical probe can be actuated while allowing the location, angle, and/or orientation of one or more components (e.g., housings, tubular members, probe heads) to be controlled.

The light source (e.g., surgical laser) included as part of a surgical probe as described herein or as part of some other surgical instrument or system (e.g., a wholly or partially automated surgical system) could include any device configured to emit a beam of illumination sufficient to cause localized heating of a target region of a biological environment (or some other environment of interest) proximate to where the emitted beam intersects with the biological environment (e.g., at a focus of the beam of illumination). The light source could include a $CO_2$ laser, a semiconductor diode laser, a dye laser, an excimer laser, a fiber laser, a gas laser, a free electron laser, or some other type or types of laser. The light source could include optical elements configured to affect one or more properties of the beam of light emitted by the surgical laser, e.g., lenses, mirrors, diffraction gratings, volume holographic gratings, collimators, nonlinear optical elements (e.g., frequency doubling or tripling media), or other elements. For example, the surgical laser could include a collimator configured to cause the beam of light to have a specified width.

The light source could be configured such that one or more properties of the beam of illumination has a specified value. For example, the light source could be configured such that a wavelength of the beam of illumination is a specified wavelength. The specified wavelength could be specified according to an application. For example, the specified wavelength could be an absorption wavelength of hemoglobin such that the beam of light preferentially heats blood. In another example, the specified wavelength could be an absorption wavelength of water in biological tissue such that the beam of light generally heats biological tissue. In another example, the specified wavelength could be an absorption wavelength of a contrast agent that is configured to bind to cancer cells such that the beam of light preferentially heats cancer cells and/or tumors. Additionally or alternatively, the specified wavelength could be a wavelength that is not substantially absorbed by a tissue to be spared during a surgical intervention. Other specified wavelengths and/or specified other properties of the beam of light emitted by a surgical laser are anticipated.

FIG. 2 illustrates, in cross-section, elements of an example surgical probe 200. The end of the surgical probe 200 comprises a probe head 210 configured to be inserted into a body cavity and from which a beam of illumination 225 can be emitted to, e.g., ablate biological tissue in the body cavity. The beam of illumination 225 is generated by a light source (not shown) and transmitted through the surgical probe 100 (e.g., via an optical fiber, through free space, through relay optics, or by some other means) to optical elements disposed in the probe head 210. The beam of illumination 225 could be emitted from the probe head 210 via a transparent window, an aperture, or some other means. FIG. 2 illustrates a mirror of the surgical probe 200 during first 221a and second 221b periods of time and a lens of the surgical probe 200 during first 223a and second 223b periods of time. Correspondingly, the location of a focus of the emitted beam of illumination is shown during the first 220a and second 220b periods of time.

The mirror 221a/b and lens 223a/b are configured to have axial locations along a longitudinal axis 230 of the surgical probe 200 that are controllable by one or more actuators. Controlling the axial location of the mirror between the first 221a and second 221b locations during respective periods of time causes the location of the focus of the emitted beam of illumination 225 to change from the first 220a to the second 220b locations along a first direction 201 parallel to the longitudinal axis 230 of the surgical probe. Controlling the axial location of the lens relative to the location of the mirror 221a/b, along the path of the beam of illumination 225, between the first 221a and second 221b locations during respective periods of time causes the location of the focus of the emitted beam of illumination 225 to change from the first 220a to the second 220b locations along a second direction 203 perpendicular to the long axis of the surgical probe such that the distance between the location of the focus 220a/b of the beam of illumination 225 and the probe head 210 is controlled. Further, the probe head 210, mirror 221a/b, or other elements of the surgical probe 200 could be rotated 215 about longitudinal axis 230 to control the location of the focus 220a/b of the beam of illumination.

FIG. 2 illustrates the linear actuation of example optical elements (e.g., a mirror 221a/b and lens 223a/b) to control the location of a focus of an emitted beam of illumination relative to a probe head. In the illustrated example, actuation of a particular optical element could cause the location of the focus to be changed in multiple directions. For example, changing the location of the mirror 221a/b while maintaining the lens 223a/b at a specified location could cause the location of the focus to move parallel to the longitudinal axis 230 in the first direction 201 as well as changing the distance between the focus and the probe head (i.e., the location of the focus along the second direction 203) by changing the distance along the path of the beam of illumination 225 between the lens 223a/b and the mirror 221a/b. In some examples, a lens, mirror, and/or other optical elements could be actuated in common. For example, a lens and mirror could be incorporated into an optical assembly having a location that can be changed (e.g., along a longitudinal axis of a surgical probe) to control the location of a focus of an emitted beam of illumination parallel to the change in location of the optical assembly while a distance between the location of the focus and the optical assembly remains substantially constant.

One or more optical elements of a surgical probe could have an angle and/or orientation that is controlled independently of the one or more optical elements having a location that is controlled (as illustrated in FIG. 2). Further, such optical elements could be used to allow other applications, e.g., to control the direction or other properties of emitted beams of light used to illuminate tissue for other purposes (e.g., to illuminate the tissue to detect a property of the tissue) and/or to control a region of sensitivity (e.g., a field of view) of a light sensor (e.g., a visible, infrared, ultraviolet, or otherwise light-sensitive element or plurality of such elements, e.g., a camera) by reflecting, refracting, or otherwise affecting light that is received from the environment of the probe and directed (e.g., by such controlled optical elements) to the light sensor.

FIG. 3 illustrates, in cross-section, elements of an example surgical probe 300. The end of the surgical probe 300 comprises a probe head 310 configured to be inserted into a body cavity and from which a beam of illumination 357 can be emitted to, e.g., ablate biological tissue 305 in the body cavity. The beam of illumination 357 is generated by a light source (not shown) and transmitted through the surgical probe 300 via an optical fiber 355 to a mirror 321 disposed in the probe head 310. The beam of illumination 357 is reflected by the mirror 321 to a particular region of tissue 320. The beam of illumination 357 could be emitted from the probe head 310 via a transparent window, an aperture, or some other means. The angle of the direction in which the beam of illumination 357 is emitted from the surgical probe 300, relative to the probe head 310, could be controlled by controlling the angle of the mirror 321 (e.g., using an actuator). This could allow control of the location of the particular region of tissue 320 to be controlled by controlling the angle of the mirror 321, by rotating 315 the probe head 310 and/or elements therein, or by operating some other element(s). Further, emitted light 337 from the particular region of tissue 320 is reflected by the mirror 321, refracted by a prism 339, and transmitted to a light sensor (not shown) by a second optical fiber 335.

The light sensor could include one or more light-sensitive elements configured to detect the amplitude or other properties of the emitted light 337 received via the mirror 321, prism 339, and optical fiber 335. In some examples, the optical elements (e.g., 321, 339, 335, or additional lenses, apertures, mirrors, gratings, or other optical elements) could be configured such that the biological tissue 305 proximate the particular region of tissue 320 could be imaged; that is, such that image information across a portion of tissue is preserved and transmitted via the optical elements to the light sensor. Additionally or alternatively, the optical elements could be configured such that only light from a specified area (e.g., a specified small area coincident with the particular region of tissue 320) and/or having some other specified property (e.g., light within a specified range of wavelengths) is relayed to the light sensor. The light sensor could be configured and/or operated to detect emitted light 337 from the biological tissue 320 that is emitted responsive to illumination by the beam of illumination 357 (e.g., a beam of illumination configured to ablate part of the biological tissue, a beam of illumination configured to excite a fluorophore in the biological tissue, or a beam of illumination configured according to some other application); additionally or alternatively, the light sensor could be configured and/or operated to detect emitted light 337 from the biological tissue 305 when the surgical probe 300 is not being operated to illuminate the biological tissue.

In some examples, the surgical probe 300 could be configured and/or operated to determine the location and/or shape of biological tissue in a body cavity. For example, the surgical probe 300 could include a camera or other multi-pixel imager configured to image the biological tissue 305 (either by being disposed on or within the probe head 310 or by being optically coupled to the optical fiber 335). The location of the particular region of tissue 320 relative to the probe head 310 could be determined by emitting the beam of illumination 357 and using triangulation or some other method to determine the location of the particular region of tissue and/or to determine the location of other regions of the biological tissue 305. Such a determination could be used to control the location and/or distance of the focus of a tissue-ablating beam of illumination emitted by the surgical probe 300 relative to the probe head 310. Further, such location information could be determined before, during, and/or after the operation of the surgical probe 300 to ablate part of the biological tissue 300 according to an application, e.g., to determine an extent of tissue ablation, to determine control a property (e.g., a power level) of a tissue-ablating beam of emitted illumination, or some other application.

One or more light-sensitive elements of the light sensor could be configured to detect the amplitude or other properties of the emitted light 337 within one or more respective ranges of wavelengths. That is, the surgical probe 300 could be configured to act as a spectrometer (or as part of a spectrometer), receiving light from the biological tissue 305 and outputting information related to the spectrum of the received light (i.e., outputting information relating to the spectrographic content of the received light). This could include the light sensor and/or other optical elements of the surgical probe 300 (e.g., 321, 339, 335) incorporating a prism and a linear (or otherwise arranged) array of light sensitive elements (e.g., photodiodes, phototransistors, pixels of a charge-coupled device (CCD), active pixel sensors) configured such that the output of an individual light sensitive element is related to the amplitude of the received emitted light 337 light within a specified range of wavelengths.

Other configurations of the light sensor and/or optical elements (e.g., 321, 339, 335) of the surgical probe 300 could enable the detection and/or determination of the spectrographic content or other information about emitted light 337 from the biological tissue 305. For example, the light sensor could be configured to receive light of an excitation wavelength of a fluorophore that is present in the biological tissue 305 (e.g., a fluorophore configured to selectively interact with cancer cells or with some other analyte in the biological tissue 305) such that the location of the fluorophore and/or some analyte (e.g., cancer cells) related to the fluorophore could be detected in the biological tissue 305. This could include using the light sensor alone and/or using the light sensor in combination with the operation of other elements (e.g., 321, 355) of the surgical probe 300 to emit a beam of illumination (e.g., a beam of illumination at an excitation wavelength of the fluorophore) toward one or more particular regions of tissue (e.g., 320) of the biological tissue 305.

Information generated by the surgical probe 300 could include determined and/or detected spectrographic content or other optical information for a plurality of portions of the biological tissue 305, identification information corresponding to the plurality of portions of the biological tissue 305 based on such determined spectrographic content or other information, an image generated based on determined and/or detected spectrographic content, identification information, and/or other information. Such information could be used to generate one or more images of the biological tissue 305, e.g., an image of tissue types of the biological tissue 305, an image of diseased regions (e.g., cancer-cell-containing regions) of the biological tissue 305. Such images could be presented to a surgeon (e.g., via a display, a head-mounted display, an augmented reality device, a display of a console used to operate a tele-surgical system) to inform a surgical intervention (e.g., operation of the surgical probe 300 to emit a beam of illumination 337 to ablate a portion of the biological tissue 305) or other actions of the surgeon. Additionally or alternatively, such images could be used to perform a surgical intervention using an automated surgical system (e.g., to automatically ablate diseased and/or cancerous tissue using the surgical probe 300).

FIG. 4 illustrates, in cross-section, elements of an example surgical probe 400. The end of the surgical probe 400 comprises a probe head 410 configured to be inserted into a body cavity and from which a beam of illumination 457 can be emitted to, e.g., ablate biological tissue 405 in the body cavity. The beam of illumination 457 is generated by first and second light sources (not shown) and transmitted through the surgical probe 300 via respective optical fibers 455, 433 to combining optics 425 that combine the light emitted by the two light sources into the beam of illumination 457 and that are disposed in the probe head 410. The beam of illumination 457 is reflected by first 421a and second 412b mirrors to a particular region of tissue 420. The beam of illumination 457 could be emitted from the probe head 410 via a transparent window, an aperture, or some other means. The angle of the direction in which the beam of illumination 457 is emitted from the surgical probe 400, relative to the probe head 410, could be controlled by controlling the angle of the first 421a and second 421b mirrors (e.g., using actuators). This could allow the location of the particular region of tissue 420 to be controlled by controlling the angles of the mirrors 421a, 421b, by rotating the probe head 410 and/or elements therein, or by operating some other element(s). Further, emitted light 437 from the particular region of tissue 420 is collected by collection optics 436 and transmitted to a light sensor (not shown) by an optical fiber 435.

Note that the first and second light sources could generate beams of illumination having different properties, could be operated during different periods of time, or could be otherwise differently configured. For example, the first light source could emit a high-power beam of illumination configured to ablate biological tissue 420 (e.g., to ablate the particular region of tissue 420, to be absorbed by water, hemoglobin, or other specified components of the tissue) and the second light source could be configured to illuminate the biological tissue 420 such that one or more properties of the biological tissue 420 and/or regions thereof could be determined (e.g., such that a location, presence of a fluorophore, a disease state, an oxygenation state, an emission, excitation, absorption, or other spectrum could be detected and/or determined) in combination with one or more sensors (e.g., the light sensor coupled to the optical fiber 435 and/or some other light sensor configured to receive emitted light 437 from the biological tissue 420).

Further, the first and second light sources could generate light during alternative or otherwise non-overlapping periods of time. For example, the second light source could, during a first period of time, generate light to illuminate the particular region of the biological tissue 420 with the beam of illumination 457 such that a location, presence of a fluorophore or other marker, health state, color, or other property of the particular region of the biological tissue 420 could be detected and/or determined (e.g., using a light source configured to receive responsively emitted light 437 via the collection optics 436 and optical fiber 435). Responsive to a determination, based on such detected and/or determined properties, that the particular region of biological tissue 420 contains a target to be ablated, the first light source, could, during a subsequent period of time, operate to generate light to illuminate the particular region of the biological tissue 420 with the beam of illumination 457 such that the particular region of the biological tissue 420 is ablated.

Note that the light from two (or more) light sources could additionally or alternatively be combined by some other optical elements and transmitted to the probe head 410 via a single optical fiber. In some examples, properties of the first 455 and second 433 optical fibers could be specified relative to respective applications of the optical fibers 455/433 to deliver respective beams of illumination. For example, the first optical fiber 455 could have a larger numerical aperture such that a higher-power beam of tissue-ablating illumination could be efficiently transmitted. Conversely, the second optical fiber 433 could be have a lower numerical aperture such that a narrower beam of tissue-scanning illumination could be translated, allowing the surgical probe 400 to detect and/or determine properties (e.g., location, health state, presence of a fluorophore) of small regions of the biological tissue 420. This could allow the mapping and/or imaging of the biological tissue 420 at a high resolution.

In some examples, multiple optical or other components of a surgical probe could be combined and/or actuated in common. For example, optical fibers, lenses, or other optical elements could include mirrored, roughened, notched, grated, or otherwise altered surfaces. Further, such combined elements (e.g., a combined optical fiber and mirror composed of an optical fiber having a mirrored surface at one or both ends) could be adjusted, affected, or otherwise actuated to control a location of a focus, a direction of emission, or other properties of a beam of illumination emitted by a surgical probe. As an example, FIG. 5 illustrates, in cross-section, elements of an example surgical probe 500. The end of the surgical probe 500 comprises a probe head 510 configured to be inserted into a body cavity and from which a beam of illumination 557 can be emitted to, e.g., ablate biological tissue in the body cavity. The beam of illumination 557 is generated by a light source (not shown) and transmitted through the surgical probe 500 via an optical fiber 555 to the probe head 510. The beam of illumination 557 could be emitted from the probe head 510 via a transparent window, an aperture, or some other means. FIG. 5 illustrates that the optical fiber 555 includes a mirrored, beveled end 556 configured to reflect illumination transmitted through the optical fiber 555 out of the surgical probe 500.

The mirrored end 556 is configured to have an axial location along a longitudinal axis of the surgical probe 500 that is controllable by one or more actuators. This could include actuating the entire optical fiber 555 and/or a segment thereof (e.g., an actuator could apply forces and/or displacements to the end of the optical fiber 555 to control the axial location of the mirrored end 556). Controlling the axial location of the mirrored end 556 causes the location of the focus 520 of the emitted beam of illumination 557 to change along a direction 517 parallel to the longitudinal axis of the surgical probe 500. Further, the probe head 510, mirrored end 556 and/or optical fiber 555, or other elements of the surgical probe 500 could be rotated 515 to control the location of the focus 520 of the beam of illumination 557 in a direction into/out of the plane of FIG. 5.

Note that the mirrored end 556 could be formed by a variety of methods. For example, a reflective substance (e.g., aluminum, silver) could be sputtered, painted, or otherwise applied to a beveled surface formed at the end of the optical fiber 555. In another example, a mirror could be formed and adhered or otherwise mounted to the optical fiber 555. In yet another example, the end of the optical fiber could be beveled and polished to provide a reflective surface. The mirror 556 could be flat or could have some other shape; for example, the mirror could have a concave or otherwise curved shape to focus the beam of emitted illumination 557. Further, note that additional or alternative reflective or otherwise optically active elements or features could be added and/or formed on or within the optical fiber 555. For example, one or more notches, gratings, roughened surfaces, or other features could be formed on or within the optical fiber 555. The optical fiber 555 (or other optical fibers illustrated herein) could include a fiber Bragg grating to filter light transmitted through the optical fiber 555.

The configuration and/or operation of surgical probes as described herein to illuminate and/or ablate specified regions of biological tissue with beams of illumination are intended as non-limiting examples. A variety of shapes and sizes of regions of biological tissue (e.g., spots, lines, or other shapes of a surface of a biological tissue) could be illuminated by a beam of illumination emitted by a surgical probe. Further, such beams of illumination could have a controllable wavelength, power, focal length, coherence, pulse frequency, or other properties according to an application.

A surgical probe (e.g., 100, 200, 300, 400, 500) or components thereof (e.g., a probe head or other housing or assembly) could be configured to rotate, translate, or otherwise move such that a region illumination and/or imaged by the surgical probe could be controlled and/or changed. Further, elements of a surgical probe (e.g., one or more actuated mirrors, lenses, or other elements) could be configured to illuminate and/or image tissue within a specified volume or area relative to the surgical probe (e.g., to illuminate and/or image tissue within a field of view defined relative to a probe head), and surgical probe or elements thereof could be configured to control the location of such a specified volume or area relative to a biological tissue or other environment or target of interest (e.g., to scan a probe head past an area of biological tissue such that every region of the area of biological tissue is location within the field of view of the surgical probe during at least one point in time). For example, the surgical probe could be mounted on a gimbal. Movement of the surgical probe and/or elements thereof (e.g., a probe head) could be effected by servos, galvanometers, motors, or some other mechanical actuator(s). In some examples, motions of the surgical probe could be controlled to automatically track a target area of biological tissue. In some examples, the surgical probe could be manually moved such that a field of view of the surgical probe includes a target region. For example, the surgical probe could be positioned at the beginning of a surgical intervention to image a target area of a biological tissue.

Figure 6A:
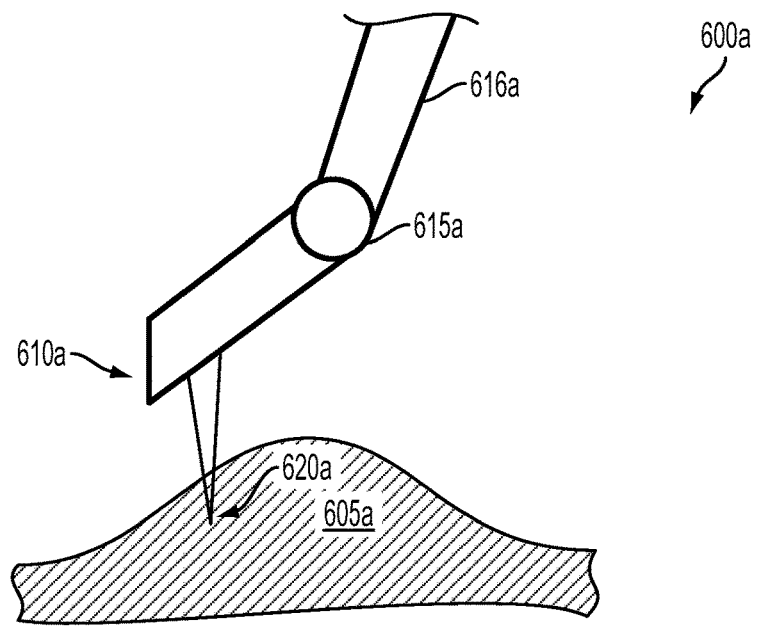
FIG. 6A illustrates a side cross-sectional view of an example surgical probe that is emitting a beam of light.

Further, the surgical probe could be articulated, flexible, or otherwise configured such that the location, angle, and/or orientation of a probe head or other element(s) of the surgical probe could be controlled. FIG. 6A illustrates elements of an example articulated surgical probe 600*a* having at least one articulation 615*a* configured to control at least an angle between a probe head 610*a* and a tubular support element 616*a* of the surgical probe 600*a*. The probe head 610*a* is configured to be inserted into a body cavity and to emit a beam of illumination 620*a* to, e.g., ablate biological tissue 605*a* in the body cavity. The location, angle, region of intersection with biological tissue, and/or other properties of the beam of illumination 620*a* relative to the location of the biological tissue 605*a* or other elements of a body of a patient could be controlled by controlling the angle between the between the probe head 610*a* and the tubular support element 616*a* (e.g., by operating a motor, hydraulic or pneumatic cylinder, or other actuator of the surgical probe 600*a*).

Figure 6B:
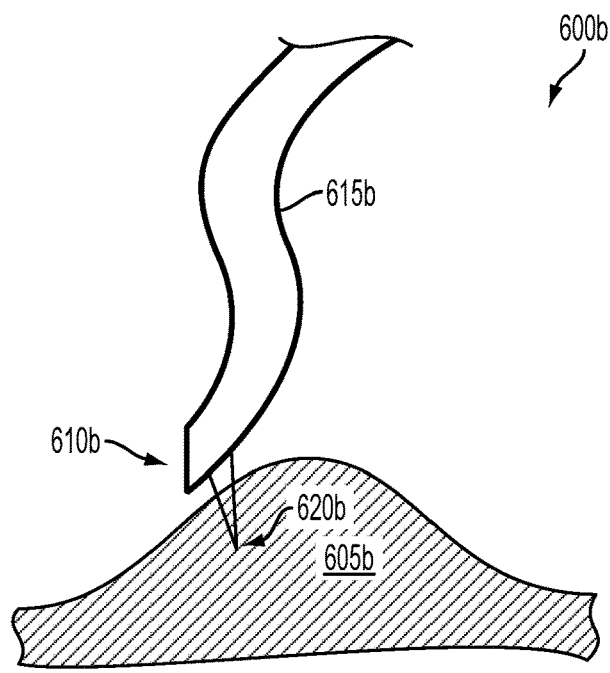
FIG. 6B illustrates a side cross-sectional view of an example surgical probe that is emitting a beam of light.

In another example, FIG. 6B illustrates elements of a flexible surgical probe 600*b* having a flexible member 615*b* configured to control a location, angle, and/or orientation of a probe head 610*b* relative to a biological tissue 605*b* or other elements in a surgical environment. The probe head 610*b* is configured to be inserted into a body cavity and to emit a beam of illumination 620*b* to, e.g., ablate biological tissue 605*a* in the body cavity. The flexible member 615*b* is configured to control at least one curvature of the flexible member 615*b* (i.e., a curvature of a specified region or length of the flexible member 615*b* in a specified direction). This could include one or more actuators configured to deform, rotate, or otherwise actuate the flexible member 615*b*. In some examples, the flexible member 615*b* could be configured similarly to a flexible endoscope probe, i.e., to include driven cables or other elements configured to exert deforming forces on or within regions of the flexible member 615*b* to control the curvature in one or more directions of the regions of the flexible member 615*b*. The location, angle, region of intersection with biological tissue, and/or other properties of the beam of illumination 620*b* relative to the location of the biological tissue 605*b* or other elements of a body of a patient could be controlled by controlling the curvature of one or more flexible regions of the flexible member 615*b* (e.g., by operating a motor, hydraulic or pneumatic cylinder, or other actuator of the surgical probe 600*b*).

Further, a surgical probe configured to control the location, angle, and/or orientation of a probe head configured to emit a beam of ablating illumination and/or of the angle of such a beam of illumination relative to such a probe head could be operated to excise, resect, dissect, or otherwise cut biological tissue. For example, such a surgical probe could be operated to dissect and/or incise a biological tissue to, e.g., access a deeper tissue covered by an overlying tissue. In another example, such a surgical probe could be operated to wholly or partially dissect around a portion of tissue to be removed, e.g., a solid tumor, a portion of tissue to be biopsied, a cardiovascular anastomosis, a cyst, or some other target tissue or structure.

As an example, FIGS. 7A-7D illustrate the operation of an articulated surgical probe 700 (that could be configured as described elsewhere herein) to dissect a biological tissue 705 such that a target 707 within the biological tissue 705 could be removed. The surgical probe 700 has at least one articulation 714 configured to control at least an angle between a probe head 710 and a tubular support element 716 of the surgical probe 700. The surgical probe 700 is further configured to control a rotation of the tubular support element 716 about a longitudinal axis of the tubular support element 716. The probe head 710 and other elements (e.g., 714, 716) of the surgical probe 700 are configured to be inserted into a body cavity and to emit a beam of illumination 720 to ablate biological tissue 705 in the body cavity. At least the angle of the beam of illumination 720 relative to the probe head 710 can be controlled (e.g., by operating a motor, hydraulic or pneumatic cylinder, or other actuator of the surgical probe 700).

FIG. 7A illustrates the surgical probe 700 and biological tissue 705 during a first period of time. The probe head 710 is positioned proximate to the surface of the biological tissue 720 containing the target 707 and the beam of illumination 720a is being directed in a direction such that it could ablate tissue around the target 707 (illustrated by the dashed line). The surgical probe 700 could be operated such that the biological tissue 705 is ablated along the direction of the beam of illumination 720a. Further, the surgical probe 700 could be operated to rotate the tubular support element 716 about a long axis of the tubular support element 716 such that the probe head 710 is rotated.

As the probe head 710 is rotated, the power, angle, or other properties of the emitted beam of illumination 720a could be controlled (e.g., by controlling a power output of a light source, by operating a mirror or other actuated optical element of the surgical probe 700) such that the biological tissue is cut along a specified surface (e.g., a conical surface) that at least partially enclosed the target 707. FIG. 7B illustrates the surgical probe 700 and biological tissue 705 during a second period of time, when such a conically-shaped cut has been partially completed in the biological tissue. A cut 725b is illustrated in the biological tissue 705 in the direction of the beam of illumination 720a of FIG. 7A; this cut represents a portion of the conical (or otherwise shaped) specified surface at least partially enclosing the target 707 that the surgical probe 700 is forming in the biological tissue 705. The surgical probe 700 is emitting a beam of illumination 720b to continue to ablate the biological tissue 705 along the specified surface.

Once the surgical probe 700 has been operated to cut the biological tissue along the specified surface (in the example of FIGS. 7A and 7B, a substantially conical surface having an apex located proximate to the surface of the biological tissue 705), the target 707 at least partially enclosed by the specified surface (and now at least partially enclosed by the corresponding cut formed in the biological tissue 705 by the surgical probe 707) could be extracted. This could include applying suction, forces, or other forces to the target 707 and/or surrounding biological tissue 705 such that the target 707 is extracted (e.g., such that the biological tissue 705 is cut, torn, dehisced, or otherwise wholly or partially removed from the biological tissue 705). Additionally or alternatively, one or more further cuts could be made, by the emitting a beam of illumination from the surgical probe 700 or through some other means (e.g., the operation of one or more manual laparoscopic and/or endoscopic instruments to cut, crush, ablate, or otherwise manipulate the biological tissue 705) to cut along a further surface such that the further surface, in combination with the original specified surface corresponding to the cut made by the surgical probe 700, fully encloses the target 707 such that the target can be extracted.

FIGS. 7C and 7D illustrate the operation of the surgical probe 700 to form a second cut along a second specified surface (e.g., a second conical surface, opposite and joined to the cut corresponding to the first specified surface, such that the surface formed from the combination of the first and second specified surfaces fully encloses the target 707). FIG. 7C illustrates the surgical probe 700 and biological tissue 705 during a third period of time. The probe head 710 is positioned within the first cut formed in FIGS. 7A and 7B, with the articulation 714 proximate to the surface of the biological tissue 720; a portion of the first cut 725c is additionally illustrated in the biological tissue 705. The beam of illumination 720c is being directed in a direction such that it could ablate tissue around the target 707 (illustrated by the dashed line). The surgical probe 700 could be operated such that the biological tissue 705 is ablated along the direction of the beam of illumination 720c. Further, the surgical probe 700 could be operated to rotate the tubular support element 716 about a long axis of the tubular support element 716 such that the probe head 710 is rotated within the first cut.

As the tubular support element 716 is rotated, the power, angle, or other properties of the emitted beam of illumination 720c could be controlled (e.g., by controlling a power output of a light source, by operating a mirror or other actuated optical element of the surgical probe 700) such that the biological tissue is cut along the second specified surface (e.g., a conical surface) that, combination with the first surface, fully encloses the target 707. FIG. 7D illustrates the surgical probe 700 and biological tissue 705 during a fourth period of time, when such a conically-shaped second cut has been partially completed in the biological tissue 705. A combined cut 725d is illustrated in the biological tissue 705; this cut represents a portion of the combination of the conical (or otherwise shaped) first and second specified surfaces at least partially enclosing the target 707 that the surgical probe 700 is forming in the biological tissue 705. The surgical probe 700 is emitting a beam of illumination 720d to continue to ablate the biological tissue 705 along the second specified surface.

Note that the use of a surgical probe with a single articulation to form one or more cut wholly or partially enclosing a target in biological tissue is intended as an illustrative example. Such a surgical probe could include more than one articulation, could include one or more flexible regions configured to have a controlled curvature or to have a shape that is controllable in some other manner, or could include some other elements configured to control the shape of the surgical probe in some other way. Alternatively, elements of the surgical probe could be disposed on or within a non-articulated, substantially rigid tubular or otherwise-shaped housing. Further, cuts in tissue could be formed in other ways and/or such cuts could be formed corresponding to specified surfaces having different relationships with the surface or other features of a biological tissue. For example, a target could be proximate to and deep from a blood vessel or other tissue or structure to be spared (i.e., a structure which should not be damaged). In such an example, a surgical probe could first act to ablate and/or cut tissue in a column, substantially perpendicular to the surface of the biological tissue and avoiding the blood vessel. The surgical probe could subsequently act to form a conical or otherwise-shaped cut from the base of such a column such a surface at least partially enclosing the target could be cut into the biological tissue without damaging the blood vessel or other tissue or structure to be spared. Other examples of operating a surgical probe to form cuts or other dissections to extract, resect, or otherwise wholly or partially remove or disable target tissues are anticipated.

Portions of tissue (e.g., portions containing tumors, neoplasms, or other targets) dissected as described above (e.g., wholly or partially cut away from an enclosing tissue) could be removed by a variety of methods. In some examples, the biological tissue within the dissection surface could be grasped (e.g., by a collection, tissue entrance, suction, or other port, or by a forceps, hemostat, clamp, or other grasping means) and removed from the body cavity. This could include placing the biological tissue within a bag or other enclosing means, and later removing the enclosing means containing the biological tissue from the body cavity. In some examples, the biological tissue could be removed via a collection, tissue entrance, or other suction port. This could include further sectioning the biological tissue (e.g., by cutting using beams of emitted illumination) such that cut portions of the further sectioned biological tissue are small enough to be removed via such a suction port. Additionally or alternatively, the dissected biological tissue could be wholly ablated within the body cavity, For example, the dissected biological tissue could be removed and/or exposed and all or part of its volume could be ablated by action of the surgical probe to emit illumination, apply electrical currents, or otherwise emit energy sufficient to wholly or partially ablate the dissected biological tissue.

Further, the use of conical specified surfaces and/or conical cuts formed in tissue are intended as non-limiting, illustrative examples. The surgical probe could be actuated (e.g., to control the angle of the beam of illumination emitted from the surgical probe) to form circular cones, elliptical cones, pyramids, or other curved cuts in biological tissue. Such cuts could be formed by rotating elements of the surgical probe about a longitudinal axis of one or more elements of the probe (as shown in FIGS. 7A-7D) or could be formed by translating, rotating, or otherwise actuating one or more elements of the surgical probe and/or by controlling one or more properties (e.g., direction, location and/or distance of a focus) of a beam of illumination emitted from the surgical probe. Further, extended flat, curved, or other surfaces could be formed by translating the probe head of a surgical probe. For example, a specified surface comprising two half-cones connected by substantially flat planes could be formed by forming a first half-cone by rotation of the surgical probe about an axis of a probe head of the probe when the probe head is disposed proximate to an apex of the first half-cone. The probe head could then be displaced laterally along the surface of the biological tissue to form a first plane. A second half-plane could then be form by rotating the probe head, and a second plane formed by displacing the probe head laterally back along the surface of the biological tissue to the apex of the first half-cone. It is anticipated that other specified surfaces could be cut into a biological tissue using a surgical probe according to similar or different operations to rotate and/or translate a probe head of a surgical probe, to control a power, location of focus, angle, or other property of a beam of tissue-ablating illumination from such a probe head, or to control other aspects of operation of the surgical probe.

A variety of mechanical apparatus could be employed to secure a surgical probe or one or more elements thereof in place relative to a target region or tissue. For example, a base of the surgical probe and/or other components could be mounted on a surgical table, a wall, a ceiling, a cart, a wearable device worn by a surgeon or other person, a surgical device or implement (e.g., to the end of a laparoscopic and/or endoscopic instrument), or to some other support. The surgical probe and/or other components could be part of some other surgical or other apparatus (e.g., an imaging system, a stereotactic surgical system, a robotic surgical system) and could be mounted to a mount, support, or other component(s) of the other surgical or other apparatus. Further, the surgical probe could include additional components, e.g., surgical lasers, robotic surgical systems, CT and/or X-ray imagers, MR imagers, ultrasonic imagers, laparoscopic and/or endoscopic systems, and/or other components according to an application. For example, the surgical probe could include multiple light sources, probe heads, collection apertures, tissue entrance ports, sensors, and/or other components.

A surgical probe as described herein, (e.g., 100, 200, 300, 400, 500, 600, 700) could include additional elements or components. The surgical probe could include one or more controllers configured to operate light sources, suction sources, collection ports, tissue entrance ports, actuators, sensors, and/or other elements of the surgical probe. The surgical probe could include communications devices (wireless radios, wired interfaces) configured to transmit/receive information to/from other systems (e.g., servers, medical imaging devices, surgical implements, surgical robots) to enable functions and applications of the surgical probe. For example, the surgical probe could include an interface configured to receive imaging information about a target environment of the surgical probe (e.g., biological tissue in a body cavity). The surgical probe could include an interface configured to present information about the surgical probe to a user and/or to allow the user to operate the surgical probe.

Additionally or alternatively, the surgical probe (or other example surgical systems described herein) could be configured to communicate with another system (e.g., a cellphone, a tablet, a computer, a remote server) and to present a user interface using the remote system. In some examples, the surgical probe could be part of another system. For example, the surgical probe could be implemented as part of a robotic surgical system (e.g., the probe head, actuators, light source, sensors, suction sources, collection ports, tissue entrance ports, and other components). That is, a surgical probe configured as described herein could be disposed as part of a robotic surgical system and could be operated as described herein. In some examples, the surgical probe could include multiple light sources (e.g., multiple lasers), multiple optical elements and/or actuators configured to adjust, affect, or otherwise actuate such, multiple probe heads or other housings or assemblies, or other additional components. The surgical probe could include a variety of sensors and/or be in communication with sensors configured to image other properties of a target environment (e.g., the biological tissue in a body cavity). Other configurations, operations, and applications of surgical probes as described herein are anticipated

IV. MAINTAINING TISSUE VISIBILITY BY A SURGICAL SYSTEM

Operation of a surgical instrument (e.g., a surgical probe as described herein) within a body cavity or other environment containing biological tissue could include the surgical instrument being exposed to a variety of fouling agents. Such fouling agents could include blood, lymph, interstitial fluid, other fluid, solid, or semi-solid matter, portions of cut or otherwise removed tissue, connective tissue, or other biological materials. Further, operation of a surgical instrument to ablate biological tissue (e.g., by direct and/or indirect application of optical, electrical, ultrasonic, or other energies) can cause the production of further fouling agents, including smoke (a mixture of gas and particulates formed by the ablation, vaporization, or other processes occurring to ablated tissue), particulates (small portions of biological tissue propelled from the site of tissue ablation by, e.g., pressures or other forces caused directly or indirectly by the ablation of tissue), or other materials.

Further, such fouling agents could act to degrade the performance of one or more processes (e.g., the further ablation of tissue) by the surgical instrument. For example, smoke or other material present in the body cavity between a surgical probe and a biological tissue to be ablated by the surgical probe could occlude the biological tissue and prevent the transmission of a beam of tissue-ablating illumination to the biological tissue. In another example, particulates, blood, or other occluding matter could be present on a window, optical elements, or other portion of the surgical probe involved in the direction of a beam of illumination toward biological tissue could prevent the transmission of such a beam of illumination to the biological tissue. Conversely, occluding matter in the body cavity and/or on elements of the surgical probe could prevent or otherwise negatively affect the detection of properties of the biological tissue through optical or other means.

A surgical probe as described herein could include one or more elements configured to remove, redistribute, or otherwise manipulate occluding matter or other fouling agents. For example, a surgical probe could include one or more collection ports that could be configured to collect smoke or other occluding materials or fouling agents by applying suction via the collection ports. Additionally or alternatively, positive pressure could be applied via one or more ports to force occluding matter (e.g., smoke) away from such surgical probes. Rinsing fluids, absorbents, wipers, scrapers, or other materials or elements could be applied to windows, optics, or other elements of a surgical probe to remove particulates or other occluding matter. Other means are anticipated for the removal of occluding matter from surfaces of a surgical probe and/or from the environment (e.g., the region within a body cavity) surrounding a surgical probe.

Figure 8A:
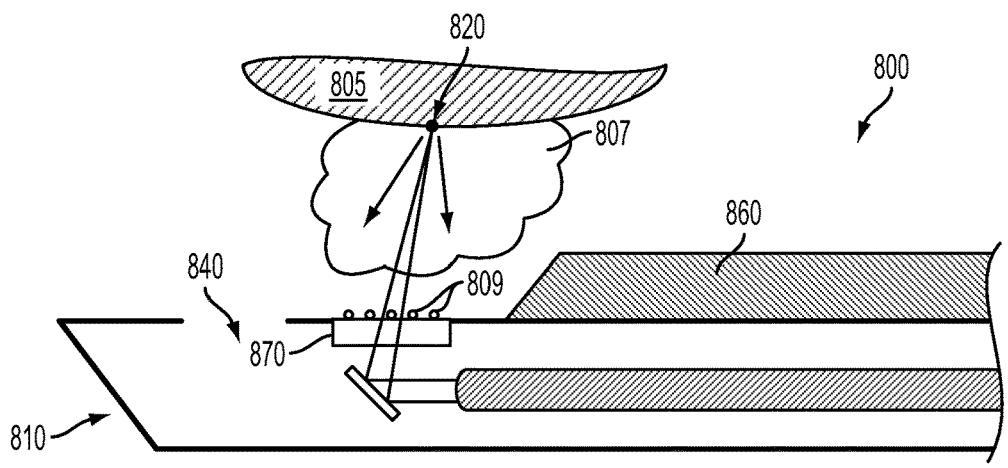
FIG. 8A illustrates a side cross-sectional view of an example surgical probe that is emitting a beam of light toward a portion of tissue containing a target tissue.
Figure 8B:
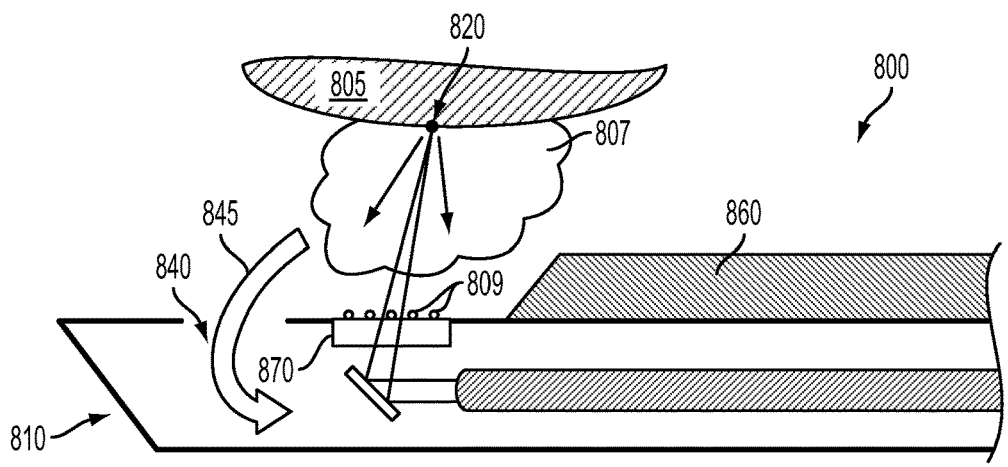
FIG. 8B illustrates a side cross-sectional view of the example surgical probe and target tissue of FIG. 8A.

As an example, FIGS. 8A-8B show a surgical probe 800 performing a surgical intervention (i.e. ablating a particular region of biological tissue 820) on a biological tissue 805. The surgical probe 800 is configured to be inserted into a body cavity containing and/or including the biological tissue 805 such that the location of a probe head 810 (i.e., a housing, assembly, or other element(s) located at the end of the surgical probe) relative to biological tissue (e.g., 805) within the body cavity can be controlled. The surgical probe 800 includes a light source (e.g., a laser, not shown) configured to emit illumination capable of ablating biological tissue. The light source is optically coupled, via an optical fiber, mirror, and/or other optical elements of the surgical probe 800 such that the beam of illumination is emitted toward the particular region of tissue 820.

The surgical probe 800 additionally includes a collection port 840 coupled to a suction source (not shown) that is configured to collect material produced by ablation of biological tissue (e.g., smoke, fluids, particulates) by beams of illumination emitted by the surgical probe 800. The beam of illumination is emitted from the surgical probe 800 via a window 870. The surgical probe 800 additionally includes a scraper 860 configured to scrape, wipe, clear, or otherwise displace occluding matter (e.g. blood, particulates) from an external surface of the window 870. As shown in FIG. 8A, the operation of the surgical probe 800 to ablate the particular region of biological tissue 820 causes the production of at least smoke 807 between the surgical probe 800 and the biological tissue 805 and particulates 809 that are deposited at least on an external surface of the window 870. The window could include anti-reflective coatings or be otherwise configured to allow beams of illumination to be efficiently transmitted through the window 870, FIG. 8B illustrates the operation of the surgical probe 800 to collect the smoke 807 produced by ablation of the biological tissue 805. Suction is applied, via the collection port 840, such that material produced by ablation of the biological tissue 805 (e.g., the smoke 807) is collected through the collection port 840. This flow of the smoke 807 is represented by arrow 845 in FIG. 8B. As shown in FIG. 8B, such collection could occur while the surgical probe 800 is operating to emit a beam of tissue-ablating illumination. Additionally or alternatively, such collection could occur when the surgical probe is not emitting tissue-ablating illumination toward the biological tissue 805. Internal structures of the surgical probe 800 (not shown) could be configured to prevent contamination of optical elements or other components of the surgical probe 800 (e.g., optical fibers, mirrors, lenses, actuators) by smoke or other materials collected via the collection port 840.

Figure 8C:
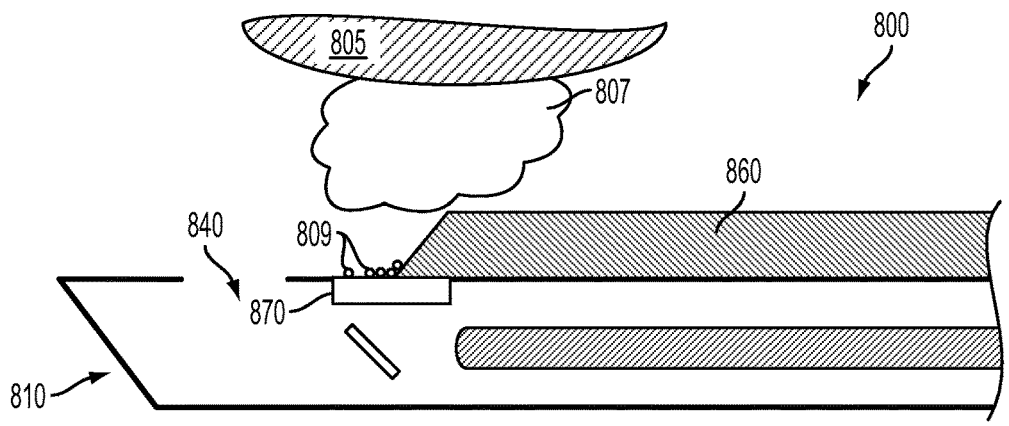
FIG. 8C illustrates a side cross-sectional view of the example surgical probe and target tissue of FIG. 8A.

As shown in FIGS. 8A-8C, a single collection 840 port could be configured and operated to provide such functionality. However, a surgical probe could include more than one such collection port. Such more than one collection port could be operated together (e.g., could be connected in common to a source of suction) or could be operated independently (e.g., to collect smoke in a particular direction, for example to reduce occlusion of a beam of emitted illumination being emitted toward particular location relative to the particular direction). Further, collection ports (e.g., 840) could have a variety of shapes according to an application.

The collection port 840 and/or one or more suction sources configured to provide suction through the collection port 840 could be operated in a variety of ways. In some examples, the collection port 840 could be used to provide a certain level of visibility of the biological tissue 805 by the surgical probe 800. This could include maintaining a level of optical absorbance or other property of the volume between the surgical probe 800 and the biological tissue 805 (e.g., due to the presence of the smoke 807) below a specified level. To provide such functionality, the level of optical absorbance or other property could be detected (e.g., by a light sensor, by determining a rate of ablation of the particular region of biological tissue 820 relative to a power level or other property of the beam of illumination, or by some other method) and a level of suction (e.g., a pressure differential, a mass or volume flow rate) could be provided through the collection port 840 related to the detected level of optical absorbance or other property of the volume between the surgical probe 800 and the biological tissue 805. Additionally or alternatively, a level of suction could be continuously provided (e.g., set to a specified level) and/or controlled by a surgeon.

Operation of a suction source to collect the smoke 807 or other occluding matter could be performed in combination with other systems. In some examples, a system could be provided to add and/or remove an inflating gas (e.g., carbon dioxide) into the body cavity containing the surgical probe 800 in order to maintain the volume of the body cavity, to provide access and/or visibility to one or more biological tissue (e.g., 805), or according to some other application. In such examples, a rate of inflating gas addition/subtraction from the body cavity could be controlled based at least in part on the operation of a suction source or other element to collect the smoke 807 or other occluding matter using the collection port 840. For example, the rate of inflating gas addition/subtraction from the body cavity could be offset by an amount corresponding to a rate of volume flow through the collection port 840 such that a total volume of the body cavity is unchanged by use of the collection port 840 to collect occluding matter. Other configurations or operations of the surgical probe 800 and related systems are anticipated.

Additionally or alternatively, the collection port 840 or some other port of the surgical probe 800 could be operated to provide a reverse suction (i.e., to emit air, carbon dioxide, or other gas) according to an application. In some examples, the collection port 840 or some other port of the surgical probe 800 could be operated to emit air or some other gas to push smoke 807 or other occluding matter away from the surgical probe 800 and/or to dilute the amount of the occluding matter (e.g., the smoke 807) present in the volume between the surgical probe 800 and the biological tissue 805. In some examples, such operation could be provided to clear blockages or occlusions in tubes, hoses, or other elements coupling the collection port 840 to a suction source and/or to clear a blockage or occlusion present in the collection port 840.

The particulates 809 or other occluding matter deposited on the window 870 (or on some other surface of the surgical probe 800) could be removed by operating the scraper 860 to displace the particulates 809 or other occluding matter. FIG. 8C shows the scraper 860 in the process of displacing the particulates 809 from the external surface of the window 870. This could include operating an actuator in the probe head 810 to move the scraper 860 and/or an actuator located in some other location and mechanically or otherwise coupled to the scraper 860 (e.g., via a cable, rod, or other force-transmitting element(s)). Such operation could be performed periodically (e.g., at a regular frequency in time, after a specified time or other measurement of operation of the surgical probe 800 to ablate the biological tissue 805) or in response to some determination or other factor. For example, an amount of occluding matter (e.g., particulates 809, blood) present on the window 870 could be detected, and/or a degree of occlusion due to such could be detected, and operation of the scraper 860 to remove or otherwise displace the occluding matter from the window 860 could be performed responsive to such determinations (e.g., a level of optical absorbance or other property of the window 860 and/or occluding matter deposited thereupon could be detected and the scraper 860 could be operated in a manner related to the detected level of optical absorbance or other property).

The scraper 860 could be composed of a variety of materials formed into a variety of shapes. For example, the scraper 860 could include elastic, viscoelastic, or other materials configured to form a seal against the window 860 such that substantially all occluding materials (e.g., 809) deposited on the window 870 are removed or otherwise displaced from the window 870 by the operation of the scraper 860. The scraper could have a chiseled edge, a beveled edge, a flat edge, a curved edge, or an edge having some other shape configured to displace fluids, particulates, or other occluding matter from a window. Further, a shape of the edge could be configured such that refraction of the scraper 860 does not re-apply particulates, fluids, or other occluding matter on the window 870. For example, the scraper 860 could include one or more peaks or other pointed structures such that surface tension or other forces cause collected or otherwise displaced occluding matter disposed on the scraper 860 to be distributed, upon retraction of the scraper 860, away from the window 870 and/or away from an active region (e.g., a central region through which beams of tissue-ablating illumination are transmitted) of the window 870.

The scraper 860 could be shaped and/or disposed on or within the surgical probe 800 (e.g., on or within the probe head 810) such that, when the probe head 810 is inserted into a body cavity (e.g., via an incision, trocar, natural body orifice or other volume between the body cavity and the outside of the body) the scraper 860 and/or edges thereof do not catch on biological tissue, trocars, or other materials into which the scraper 860 and/or surgical probe 800 come into contact. For example, the scraper 860 could be configured to be disposed within a cavity or storage aspect of the surgical probe 800 when the scraper 860 is not in use and/or when the surgical probe 800 is being inserted into the body cavity. In another example, the scraper 860 could be configured to cover the window 870 and to be disposed flush with an external surface of the probe head 810 when the surgical probe 800 is inserted into a body cavity such that the surgical probe 800 can be inserted without catching on biological tissue, trocars, or other materials into which the scraper 860 and/or surgical probe 800 come into contact. Additionally or alternatively, a recess in the probe head 810 in which the scraper 860 moves could have gradual edges. Other configurations and/or operations of the scraper 860, surgical probe 800, or other elements to minimize catching of elements of the surgical probe 800 on biological tissue when inserting the surgical probe 800 into a body cavity or otherwise operating the surgical probe 800 are anticipated.

As shown in FIG. 8B, the scraper 860 is configured to move over the window 870 to displace the particulates 809 and/or other occluding matter from the window, and subsequently to be refracted. However, the scraper 860 could be configured to toggle between states, e.g., to move from a first location on a first side of the window 870 (as shown) to a second location on an opposite side of the window 870 when removal of occluding matter (e.g., 809) is commanded. The scraper 870 could remain on the opposite side until a subsequent command to remove occluding matter from the window 870. In this way, the re-deposition of occluding material that is collected on the scraper 860 when retracting the scraper 860 could be avoided. Additionally or alternatively, the scraper 860 could be configured to operate in combination with the collection port 840. For example, the scraper 860 could be operated to displace occluding matter from the window to a location proximate to and/or over the collection port 840, and suction could be applied via the collection port 840 to collect the occluding matter displaced by the scraper 860.

In some examples, rinsing fluids could be applied (e.g., via the collection port 840 or some other port or aperture, not shown) to remove occluding matter from the window 870, the scraper 860, or from some other element of the surgical probe 800 and/or from a region of the biological tissue 820. Such fluids could include saline solutions (e.g., isotonic saline), solvent solutions, detergents, antibacterial or antibiotic agents, clotting or anti-clotting agents, anesthetics, drugs, or other chemicals or other substances. In some examples, the scraper 860 or some other element of the surgical probe 800 could include one or more absorbent elements configured to absorb fluids or other occluding matter from the window 870, the scraper 860, or from some other element of the surgical probe 800 and/or from a region of the biological tissue 820. Additional or alternative methods of operation of scrapers, collection ports, rinsing ports, absorbent elements, and/or other means for removing and/or displacing occluding matter or other materials or tissues present on or near the surgical probe 800 or at other locations in a body cavity are anticipated.

V. CONTROLLING THE LOCATION OF TISSUES RELATIVE TO A SURGICAL SYSTEM

Operation of a surgical probe as described herein to ablate specified regions of biological tissue and/or detect properties of such tissue could be facilitated by knowledge of the location of such tissue. However, biological tissue could be displaced, deformed, or otherwise moved during operation of such a surgical probe due to a variety of factors (e.g., breathing of a patient, other movements of a patient, pulsatile motion of tissue due to blood flow, peristalsis, or other biological processes, displacement of tissue due to the operation of the surgical probe or some other surgical instruments and/or the activities of a surgeon). Further, certain sensors and/or imaging or detection modalities could be contingent upon direct contact with biological tissue (e.g., direct contact between two or more electrodes and a portion of tissue).

A surgical probe could include a variety of means configured to secure one or more portions of tissue relative to the surgical probe and/or elements thereof (e.g., relative to an electrode, relative to the location of a focus of a beam of illumination emitted by the surgical probe). Such means could include forceps, clamps, hooks, or other means for grasping onto and/or through biological tissue. Such means could include applying sutures, adhesives, or other materials on, through, and/or between the surgical probe and the biological tissue. In some examples, suction could be applied via one or more ports to secure a portion of tissue near or within the port(s). Suction could be applied via one or more tissue entrance ports having one or more shapes, sizes, edge geometries, or other properties according to an application.

A level of suction or other properties of the applied suction could be specified according to an application, e.g., to allow a force to be exerted onto the biological tissue, to control the location of one or more portions of the tissue relative to the location of a focus of a beam of illumination emitted by the surgical probe, to cause a certain amount of dimpling or other deformation of tissue secured using the suction, or to allow some other application. Further suction could be applied at different levels during different periods of time. For example, a first level of suction could be applied during a first period of time to secure a portion of tissue, and a second, lesser level of suction (e.g., substantially no suction) could be applied during a second period of time to release the portion of tissue. In another example, a first level of suction could be applied during a first period of time to secure a portion of tissue. During a second period of time, a lesser level of suction could be applied, allowing the particular portion of tissue to be displaced from the tissue collection port but maintaining the tissue collection port in contact with neighboring regions of the biological tissue (e.g., to allow the surgical probe to 'scan' contiguous regions of tissue without sequentially securing and releasing different portions of the tissue). In another application, a level of suction could be applied (in combination with a shape, size, or other properties of a tissue collection port) to cause localized ischemia in a secured portion of tissue, e.g., to minimize blood loss during ablation or some other intervention, to allow detection of a property of the tissue (e.g., spectrographic information about the tissue in the absence of blood), to induce necrosis in the tissue (e.g., by ischemia, crush injury, or via some other mechanism), or according to some other application.

Figure 9A:
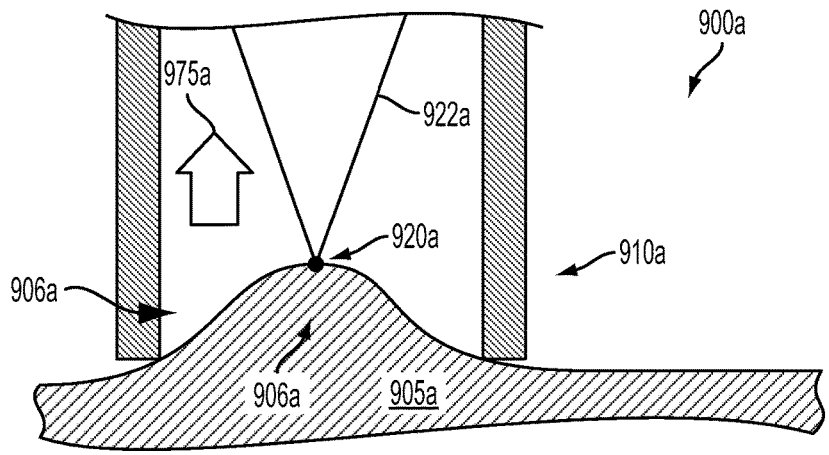
FIG. 9A illustrates a side cross-sectional view of an example surgical probe that is emitting a beam of light toward a portion of tissue that is held in place by suction applied by the example surgical probe.

FIG. 9A illustrates an example surgical probe 900a configured to secure a portion of a biological tissue 905a in a body cavity relative to the surgical probe 900a (e.g., relative to a location of a focus of a beam of illumination 922a emitted by the surgical probe 900a) by applying suction 975a via a tissue entrance port 906a. Surgical probe 900a is configured to be inserted into the body cavity such that the location of a probe head 910a (i.e., a housing, assembly, or other element(s) located at the end of the surgical probe 900a) relative to biological tissue (e.g., 905a) within the body cavity can be controlled. The surgical probe 900a additionally includes a light source (e.g., a laser, not shown) configured to emit illumination 922a capable of ablating biological tissue at a specified location (e.g., to ablate a particular region of tissue 920a).

Figure 9B:
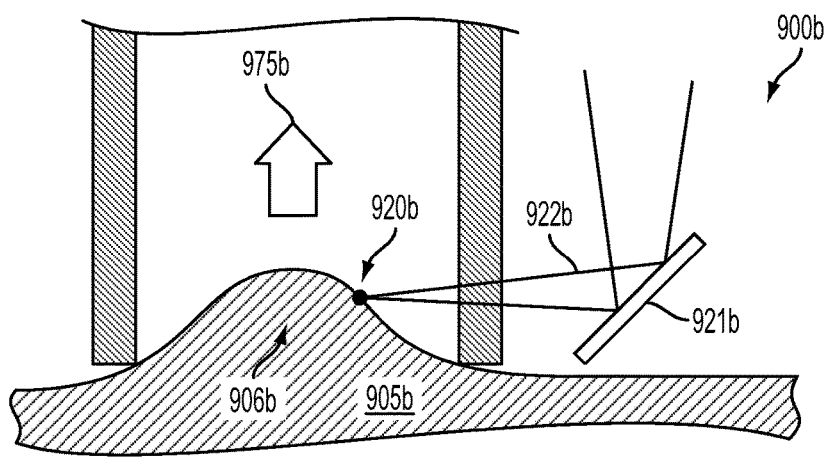
FIG. 9B illustrates a side cross-sectional view of an example surgical probe that is emitting a beam of light toward a portion of tissue that is held in place by suction applied by the example surgical probe.

As shown in FIG. 9A, the beam of illumination 922a is delivered to the biological tissue 905a along and within a volume above the tissue entrance port 906a. Additionally or alternatively, such illumination could be delivered from some other direction, for example, from a region of a surgical probe to the side of the tissue entrance port. FIG. 9B illustrates an example surgical probe 900b configured to secure a portion of a biological tissue 905b in a body cavity relative to the surgical probe 900b (e.g., relative to a location of a focus of a beam of illumination 922b emitted by the surgical probe 900b) by applying suction 975b via a tissue entrance port 906b. Surgical probe 900b is configured to be inserted into the body cavity such that the location of a probe head 910b (i.e., a housing, assembly, or other element(s) located at the end of the surgical probe 900b) relative to biological tissue (e.g., 905b) within the body cavity can be controlled. The surgical probe 900b additionally includes a light source (e.g., a laser, not shown) configured to emit illumination 922a from the side of the tissue entrance port 906b via a mirror 921b capable of ablating biological tissue at a specified location (e.g., to ablate a particular region of tissue 920a).

Figure 9C:
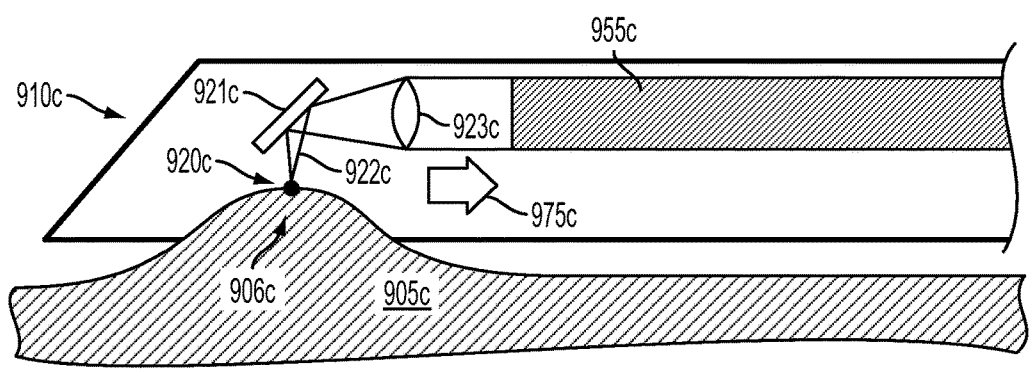
FIG. 9C illustrates a side cross-sectional view of an example surgical probe that is emitting a beam of light toward a portion of tissue that is held in place by suction applied by the example surgical probe.

In another example, FIG. 9C illustrates a surgical probe 900c. Surgical probe 900c is configured to be inserted into a body cavity containing biological tissue 905c such that the location of a probe head 910c (i.e., a housing, assembly, or other element(s) located at the end of the surgical probe 900c) and/or the location of a focus of a beam of illumination 922c emitted by the surgical probe 900c relative to biological tissue (e.g., 905c) within the body cavity can be controlled. The surgical probe 900c includes a tissue entrance port 906c through which suction 975c can be applied to secure the portion of tissue 906c relative to the probe head 910c. The surgical probe 900c additionally includes a light source (e.g., a laser, not shown) configured to emit illumination 922c capable of ablating biological tissue. The light source is optically coupled, via an optical fiber 955c, to a mirror 921c and lens 923c such that the beam of illumination 922c is emitted toward a particular region of tissue 920c of the biological tissue 905c in the body cavity.

Figure 10:
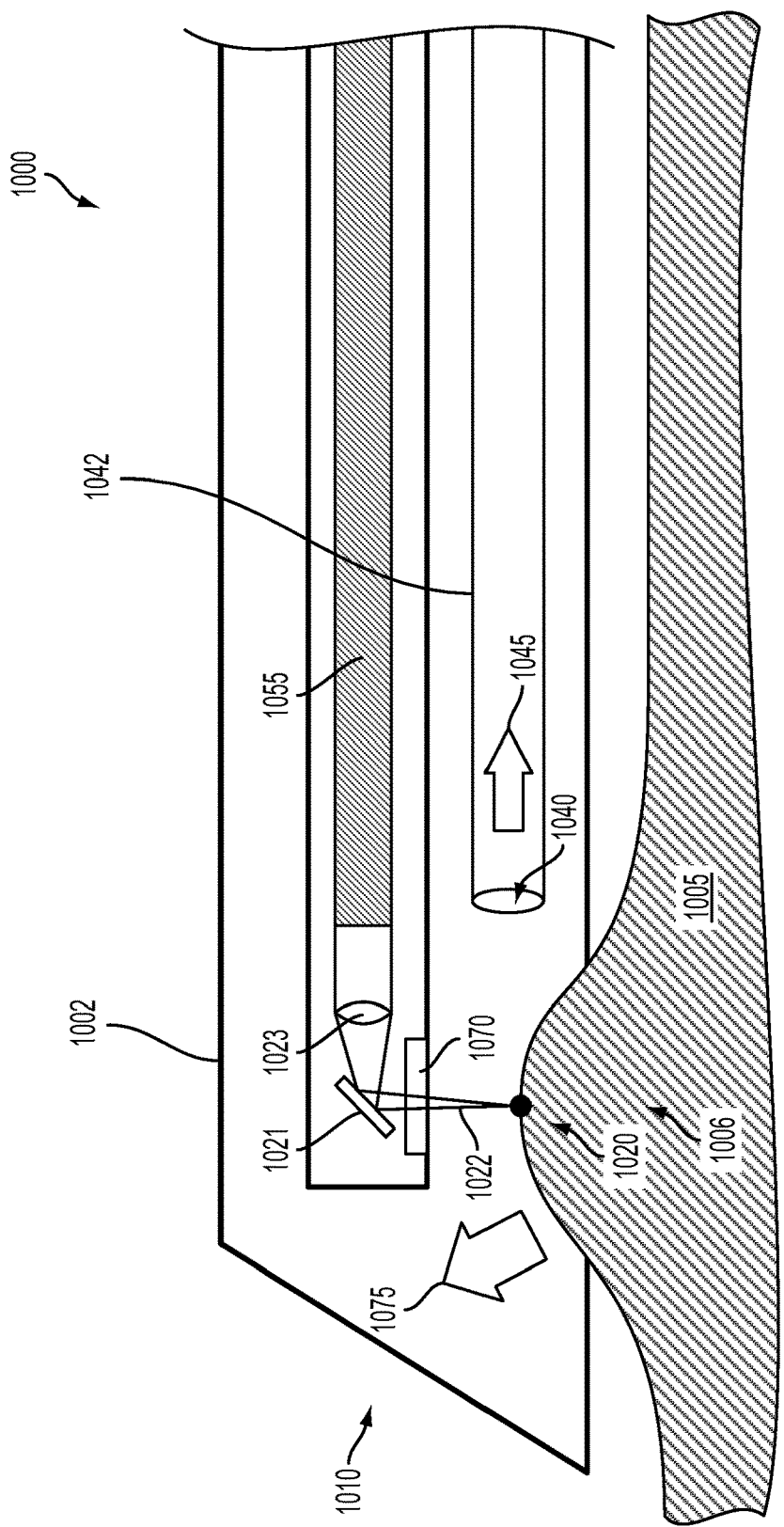
FIG. 10 illustrates a side cross-sectional view of an example surgical probe that is emitting a beam of light toward a portion of tissue that is held in place by suction applied by the example surgical probe.

Surgical probes as described herein could include multiple tissue entrance ports in addition to other elements, for example, one or more collection ports or other elements (e.g., scraper, rinsing fluid ports, absorbent elements) configured to collect, displace, or otherwise manage occluding matter (e.g., smoke, particulates, blood) located between such surgical probes and biological tissue to be ablated, imaged, sensed, displaced, or otherwise interacted with by the surgical probe. In an example, FIG. 10 illustrates a surgical probe 1000 that includes a generally tubular housing 1002. Surgical probe 1000 is configured to be inserted into a body cavity containing biological tissue 1005 such that the location of a probe head 1010 (i.e., a housing, assembly, or other element(s) located at the end of the surgical probe 1000) relative to biological tissue (e.g., 1005) within the body cavity can be controlled. The surgical probe 1000 includes a tissue entrance port 1006 in the housing 1002 through which suction 1075 (e.g., a specified differential less than and relative to a pressure of gas in the body cavity surrounding the surgical probe 1000 and biological tissue 1005) can be applied to secure the portion of tissue 1006 relative to the probe head 1010.

The surgical probe 1000 additionally includes a light source (e.g., a laser, not shown) configured to emit illumination 1022 capable of ablating biological tissue. The light source is optically coupled, via an optical fiber 1055, to a mirror 1021 and lens 1023 such that the beam of illumination 1022 is emitted, through window 1070, toward a particular region of tissue 1020 of the biological tissue 1005 in the body cavity. The surgical probe 1000 additionally includes a collection port 1040 coupled via a collection tube 1042 to a suction source (not shown) that is configured to collect material produced by ablation of biological tissue (e.g., smoke, fluids, particulates) by beams of illumination emitted by the surgical probe 1000 by applying a suction 1045 (e.g., a specified volume flow rate of gas, particulates, fluids, and/or other occluding matter) via the collection port 1040.

The collection port 1040 is configured to collect smoke or other material produced by ablation of biological tissue by beams of illumination (e.g., 1022) emitted by the surgical probe 1000. This could include providing suction continuously, providing suction during and/or after operation of the surgical probe 1000 to ablate tissue, providing suction in response to detection of an amount of produced smoke of other material produced by ablation proximate to the window 1070, providing suction in response to a detection and/or determination that the operation of the surgical probe 1000 is being degraded by the presence of materials produced by ablation of biological tissue (e.g., beam energy is being absorbed by ablated material and/or an emitted beam is being de-focused by ablated material), or providing suction according to some other consideration or factor. Further, such collection of ablated material could be performed by providing suction through a number of collection ports and/or by providing negative suction (i.e., by forcing air or other gases out of) via one or more ports. Additionally or alternatively, rinsing fluids, scraping means, absorbing means, or other elements could be provided as part of the surgical probe 1000 to remove materials produced by ablation of biological materials by the surgical probe 1000.

Tissue-securing applied suction 1075 could be provided by a suction source in addition to and/or a part of the suction source configured to provide suction via the collection port 1040. Additionally or alternatively, the surgical probe 1000 could be configured to provide suction via the collection port 1040 and further via the tissue entrance port 1006 to collect ablation material and to secure a portion of the biological tissue 1005 relative to the probe head 1010, respectively. This could include operating the surgical probe 1000 during alternating periods of time to alternatively provide suction through the tissue entrance port 1006 to secure tissue (e.g., to secure tissue during operation of the surgical probe 1000 to ablate part of the secured portion of tissue) and to collect ablated materials (e.g., after part of the secured portion of tissue has been ablated and the portion of tissue is no longer secured in the tissue entrance port 1006). Additionally or alternatively, a passive aperture, active valves, or other elements of the surgical probe 1000 could be configured and/or operated such that suction 1045 can be provided by a suction source via the collection port 1040 to collect ablated materials (e.g., to provide a specified volume flow rate through the collection port 1040) and such that suction 1075 can be provided by the suction source via the tissue entrance port 1006 such that the portion of the biological 1005 tissue is secured (e.g., by providing a specified pressure within the tissue entrance port 1006 relative to a pressure outside of the probe head 1010).

Portions of biological tissue could be secured, using suction applied via tissue entrance ports, to allow detection of properties of the biological tissue using sensors configured to detect such properties through direct contact with the tissue (e.g., through direct contact between an electrode of the surgical probe and the tissue) and/or through positioning of the sensors at a specified location and/or distance proximate to the biological tissue. Further, such positioning of biological tissue using suction (or other means) could allow for ablation of specified regions of the biological tissue in a more controlled manner, more quickly, at a higher resolution, using simpler and/or more cost-effective components, or according to some other improved consideration.

Figure 11A:
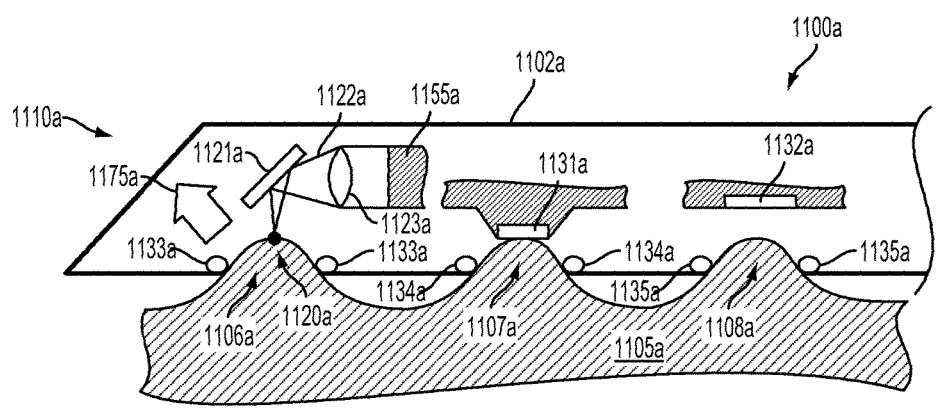
FIG. 11A illustrates a side cross-sectional view of an example surgical probe that is emitting a beam of light toward a portion of tissue that is held in place by suction applied by the example surgical probe.

FIG. 11A illustrates a surgical probe 1100a. Surgical probe 1100a includes a generally tubular housing 1102a and is configured to be inserted into a body cavity containing biological tissue 1105a such that the location of a probe head 1110a (i.e., a housing, assembly, or other element(s) located at the end of the surgical probe 1100a) relative to biological tissue (e.g., 1105a) within the body cavity can be controlled. The surgical probe 1100a includes three tissue entrance ports 1106a, 1107a, 1108a in the housing 1102a through which suction 1175a can be applied to secure portions of biological tissue 1105a relative to the probe head 1110a. The surgical probe 1100a additionally includes a light source (e.g., a laser, not shown) configured to emit illumination 1122a capable of ablating biological tissue. The light source is optically coupled, via an optical fiber 1155a, to a mirror 1121a and lens 1123a such that the beam of illumination 1122a is emitted toward a particular region of tissue 1120a of the biological tissue 1105a in the body cavity.

The surgical probe 1100a additionally includes contact sensors 1133a, 1134a, 1135a, 1131a and proximity sensor 1132a configured to detect one or more properties of biological tissue when in contact with or placed in proximity to biological tissue, respectively. Contact sensors (e.g., 1133a, 1134a, 1135a, 1131a) could include electrodes, temperature probes, mechanical sensors (e.g., active or passive sensors of stiffness, compliance, pressure, or other mechanical properties of tissue), chemical sensors, pH sensors, surface plasmon sensors, electrical impedance sensors, ion sensors, electrical potential sensors, acoustical (e.g., ultrasonic) sensors, or other types of sensors. In some examples, a contact sensor could include two or more elements in contact with tissue and/or two or more contact sensors or elements thereof could be operated in concert to detect some property of tissue. For example, first and second electrodes configured to make a direct electrical contact with a portion of tissue at two different locations and to pass an alternating current through the tissue, via the first and second electrodes, to measure an electrical impedance, an electrochemical potential, or some other property of the biological tissue). As shown in FIG. 11A, first 1133a, second 1134a, and third 1135a pairs of electrodes are configured to detect an electrical impedance of respective portions of the biological tissue 1005a secured in respective first 1106a, second 1107a, and third 1108a tissue entrance ports.

Non-contact sensors (e.g., 1132a) could include sensors configured to emit and/or receive energy (e.g., illumination, visible light, infrared radiation, ultraviolet radiation, acoustic waves and/or ultrasound) and/or fields (e.g., electric fields, magnetic fields, electromagnetic fields) to/from portions of biological tissue proximate to the non-contact sensors and/or at a specified location (e.g., within a specified volume) relative to the non-contact sensors. In some examples, optical or other elements used to illuminate biological tissue could be part of and/or operated in combination with non-contact sensors. For example, the optical elements 1121a, 1123a, 1155a, used to deliver a tissue-ablating beam of illumination could additionally or alternatively be used to deliver a beam of illumination configured to illuminate the tissue in order to optically detect the location, color, spectral properties (e.g., emission, excitation, absorption, reflection, or other spectrographic content), or other properties of the biological tissue 1105a. Light responsively emitted from biological tissue in response to such illumination (e.g., light emitted from a fluorophore in the tissue in response to illumination of the tissue with light at an excitation wavelength of the fluorophore)

Contact and/or non-contact sensors could be mounted on a rod or otherwise actuated within the probe head 1110a such that a single sensor could be used to detect properties of multiple portions of biological tissue secured by multiple respective tissue entrance ports. Additionally or alternatively, sensors could be actuated such that multiple sensors could be used alternatively to detect properties of a portion of biological tissue secured by single tissue entrance port.

Figure 11B:
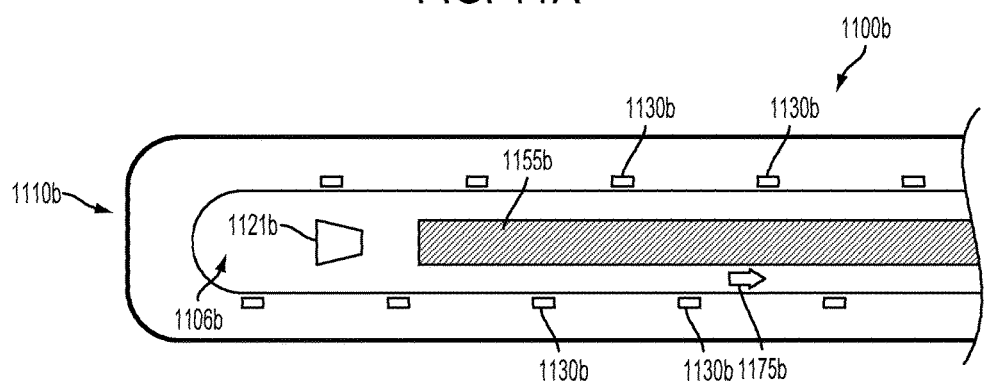
FIG. 11B illustrates a bottom view of an example surgical probe that is configured to apply suction to biological tissue to hold the biological tissue in place.

As illustrated in FIG. 11A, a surgical probe could include a plurality of tissue entrance ports having similar or different shapes. In some examples, a tissue entrance port could be elongated and/or otherwise configured to secure an extended region of tissue for an application. FIG. 11B illustrates, in bottom view, a surgical probe 1100b. Surgical probe 1100b is configured to be inserted into a body cavity containing biological tissue such that the location of a probe head 1110b (i.e., a housing, assembly, or other element(s) located at the end of the surgical probe 1100b) relative to biological tissue within the body cavity can be controlled. The surgical probe 1100b includes an elongated tissue entrance port 1106b through which suction 1175b can be applied to secure an elongated portion of biological tissue relative to the probe head 1110b. The surgical probe 1100b additionally includes a light source (e.g., a laser, not shown) configured to emit illumination capable of ablating biological tissue. The light source is optically coupled, via an optical fiber 1155b, to a mirror 1121b and/or other optical elements (e.g., a lens, not shown) such that the beam of illumination is emitted toward a particular region of tissue of the biological tissue in the body cavity that is secured in the tissue entrance port 1106b by the application of the suction 1175b. The surgical probe 1100b additionally includes an array of contact sensors 1130b that include electrodes configured to detect an electrical impedance of regions of the biological tissue along the tissue entrance port 1106b when in contact with biological tissue.

Such a surgical probe 1100b could be configured and/or operated to detect, using the electrodes 1130b and/or some other sensing means, one or more properties (e.g., a health state, a presence of cancer cells or some other target with the tissue) of the biological tissue at a plurality of points along the tissue entrance port 1106b. The surgical probe could then operate to ablate selected regions of the portion of tissue secured in the tissue entrance port 1106b. This could include actuating the mirror 1121b and/or optical fiber 1155b to control a location of an emitted beam of tissue-ablating illumination along a longitudinal axis of the surgical probe 1100b.

As noted above, a number of different sensors could be configured to detect properties of a single portion of biological tissue secured within a single tissue entrance port. Further, such multiple sensors could be configured to perform such detection alternatively by being actuated to alternatively be exposed and/or placed in contact with the single portion of biological tissue.

The use of suction applied via one or more tissue entrance ports could be used to provide a variety of applications. As noted above, such securement of portions of biological tissue could allow for the ablation of regions of the secured tissue and/or the detection of properties of such secured tissue. Additionally or alternatively, a suction source and coupled tissue entrance port could be used as a gripper or to otherwise enable manipulation of biological tissue by a surgical probe, e.g., to separate tissues that have been dissected, to place into proximity portions of biological tissue to be joined (e.g., by adhesives, sutures, or some other means), to extract a dissected portion of tissue (e.g., a biopsy sample, a tumor or other target in tissue), or the allow some other applications. Additional configurations and applications of surgical probes and elements or components thereof as described herein are anticipated.

VI. EXAMPLE SURGICAL SYSTEM

Figure 12:
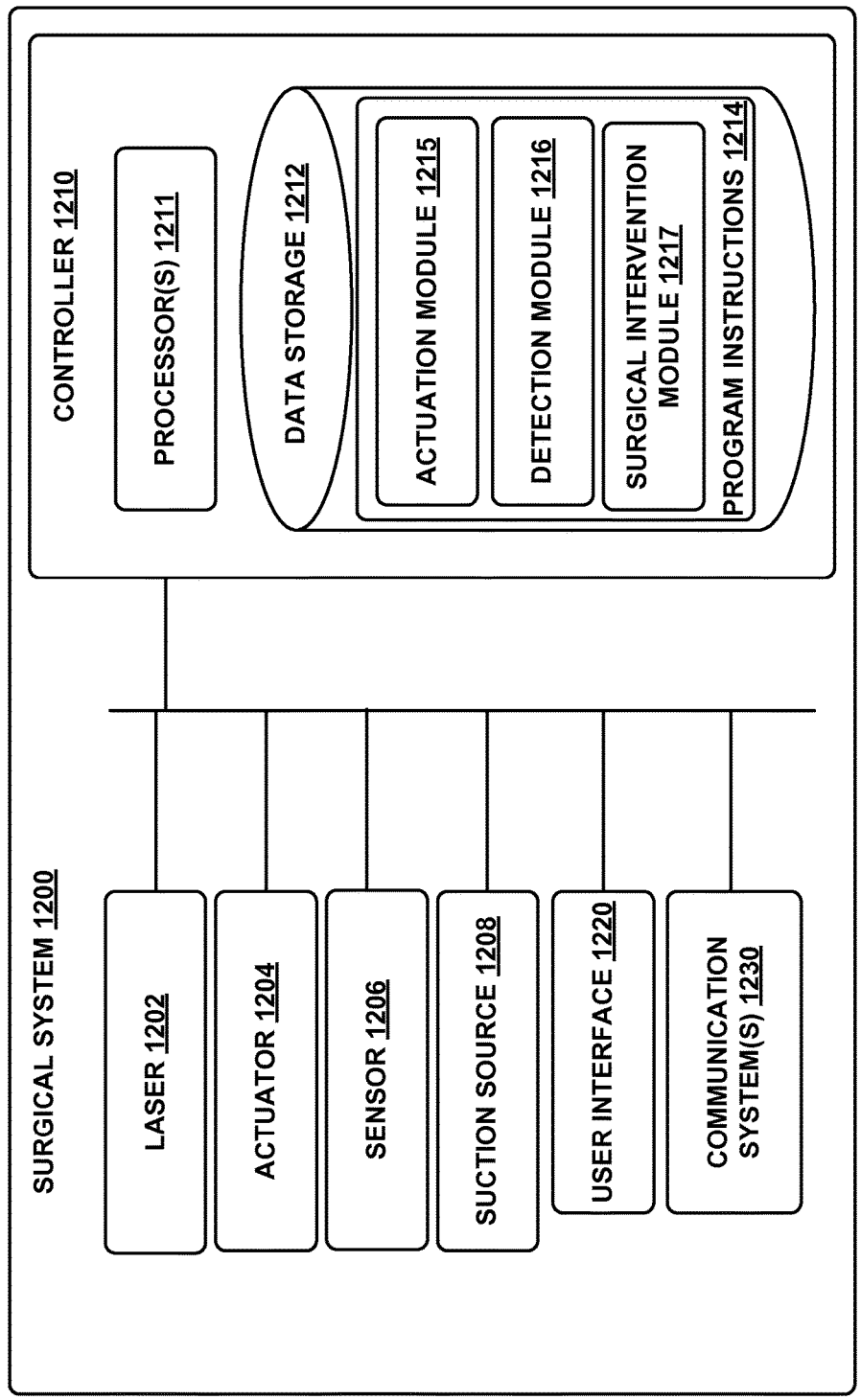
FIG. 12 is a functional block diagram of an example surgical system.

FIG. 12 is a simplified block diagram illustrating the components of a surgical system 1200, according to an example embodiment. Surgical system 1200 may take the form of or be similar to one of the example surgical probes 100, 200, 300, 400, 500, 600a, 600b, 700, 800, 900a, 900b, 900c, 1000, 1100a, 1100b, and 1100c shown in FIGS. 1, 2, 3, 4, 5, 6A, 6B, 7A-C, 8A-C, 900A, 900B, 900C, 1000, 1100A, 11B, and 1100C. Surgical system 1200 may take a variety of forms, such as a wall, surgical table, ceiling, or floor-mounted device. Surgical system 1200 could also take the form of a system, device, or combination of devices that is configured to part of another device, apparatus, or system. For example, surgical system 1200 could take the form of a surgical probe, suction source, light source (e.g., surgical laser), and/or other components configured to be mounted to or otherwise disposed as part of a surgical apparatus, tool, implement, or system (e.g., a robotic surgical system, a stereotactic surgical apparatus, a laparoscopic and/or endoscopic surgical system). Surgical system 1200 could also take the form of a system configured to ablate, detect properties of, or otherwise manipulate and/or interact with some other industrial environment, medical environment, scientific environment, or some other environment. Surgical system 1200 also could take other forms.

In particular, FIG. 12 shows an example of a surgical system 1200 having a laser 1202, an actuator 1204, a sensor 1206, a suction source 1208, a user interface 1220, communication system(s) 1230 for transmitting data to a remote system, and controller 1210. The components of the surgical system 1200 may be disposed on or within a mount or housing or on some other structure for mounting the system to enable stable tissue ablation, tissue imaging, or other functions relative to elements in a surgical environment of interest, for example, to a surgical frame secured relative to a biological tissue located within a body cavity that is subject to a surgical intervention. The surgical system 1200 could include additional components.

Controller 1210 may be provided as a computing device that includes one or more processors 1211. The one or more processors 1211 can be configured to execute computer-readable program instructions 1214 that are stored in a computer readable data storage 1212 and that are executable to provide the functionality of a surgical system 1200 as described herein.

The computer readable data storage 1212 may include or take the form of one or more non-transitory, computer-readable storage media that can be read or accessed by at least one processor 1211. The one or more computer-readable storage media can include volatile and/or non-volatile storage components, such as optical, magnetic, organic or other memory or disc storage, which can be integrated in whole or in part with at least one of the one or more processors 1211. In some embodiments, the computer readable data storage 1212 can be implemented using a single physical device (e.g., one optical, magnetic, organic or other memory or disc storage unit), while in other embodiments, the computer readable data storage 1212 can be implemented using two or more physical devices.

The laser 1202 is configured to emit a beam of illumination capable of ablating biological tissue. The laser 1202 could include a 2 micron laser, a $CO_2$ laser, a semiconductor diode laser, a dye laser, an excimer laser, a fiber laser, a gas laser, a free electron laser, or some other type or types of laser. The surgical laser 1202 could include optical elements configured to affect one or more properties of the beam of light emitted by the laser, e.g., lenses, mirrors, diffraction gratings, volume holographic gratings, collimators, nonlinear optical elements (e.g., frequency doubling or tripling media), or other elements. Further, the laser 1202 could include multiple light-emitting elements (e.g., multiple $CO_2$ lasers, multiple dye lasers, multiple lasers of different types) configured to emit a beam in common (e.g., by the use of beam combiners, beam splitters, dichroic mirrors or other elements, gratings, or other optical components). Additionally or alternatively, the surgical system 1200 could include additional lasers (not shown).

The actuator 1204 is configured to control the location of a focus of the beam of illumination emitted by the laser 1202 by controlling at least one optical element (e.g., a mirror, a lens) that is optically coupled to the laser 1202. The actuator 1204 could be configured in a variety of ways to control the location of the focus of beams of light emitted by the laser 1202, for example, controlling the location, orientation, or other properties of the at least one optical elements coupled to the laser 1202. Additionally or alternatively, the actuator could act to control a location, orientation, or other properties of the surgical system 1200 and/or of housings or subcomponents (e.g., a probe head) thereof. For example, the surgical system could include a probe head configured to be inserted in a body cavity and from which the beam of illumination is emitted, and the actuator 1204 could be configured to control the location, angle, orientation, or other properties of the probe head and/or of optical elements disposed within the probe head. The actuator 1204 could include electromechanical motors, galvanometers, solenoids, or other elements configured to control one or more elements of the surgical system 1200 by producing a magnetic field. Additionally or alternatively, the actuator 1204 could include electrostatic elements, piezoelectric elements, electrowetting elements, bimetallic or other thermally-deformable elements, or some other elements. Further, the actuator 1204 could include hydraulic, pneumatic, or otherwise fluid-controlled elements.

The sensor 1206 is configured to detect a property (e.g., a health state, a presence of cancer cells, a presence of a fluorophore) of biological tissue proximate to the surgical system 1200, e.g., proximate to a probe head of the surgical system 1200. The sensor could include optical sensors (e.g., one or more light-sensitive elements configured to detect visible, infrared, ultraviolet, or other light), electrical sensors (e.g., sensors configured to detect an electrophysiological potential across tissue and/or an electrical impedance of the tissue), electrochemical sensors (e.g. pH sensors, ion sensors, analyte sensors), or some other type of sensor(s). In some examples, the sensor 1200 could be configured to operate in concert with the actuator 1204, surgical laser 1202, and/or other elements of the surgical system 1200. For example, a sensing light source (e.g., a laser or other light-emitting element configured to emit a beam of light to, e.g., excite fluorophores in biological tissue) could be configured to emit light using optical elements (e.g., optical fibers, mirrors, lenses) in common with the laser 1202 such that the sensing light source illuminates the same region of tissue that could be ablated by operation of the laser 1202. Other configurations and operations of the sensor 1206 are anticipated (e.g., as described elsewhere herein).

The suction source 1208 is configured to provide suction (e.g., a specified pressure, a specified volume flow rate of gas, fluids, and/or particulates) through a collection port of the surgical system 1200. The collection port is configured to collect occluding matter (e.g., smoke, particulates, blood, or other materials) from between the surgical system 1200 (e.g., from a window of the surgical system 1200 from which a beam of tissue-ablating illumination is emitted) and a biological tissue being ablated, detected, manipulated, or otherwise interacted with by the surgical system 1200.

The program instructions 1214 stored on the computer readable data storage 1212 may include instructions to perform any of the methods described herein. For instance, in the illustrated embodiment, program instructions 1214 include an actuation module 1215, a detection module 1216, and a surgical intervention module 1217.

The actuation module 1215 can include instructions for operating the actuator 1204 to control the location of a focus of a beam of light emitted from the surgical system, as described herein. Generally, instructions in the actuation module 1215 describe methods of operating the actuator 1204 to control the angle, location, orientation, direction, focal distance, or other properties of a beam of illumination emitted by the surgical system 1200 (e.g., a beam of tissue-ablating illumination, a sensing beam of fluorophore-exciting illumination) to correspond to the location of one or more particular portions of biological tissue during one or more respective periods of time. Other operations, functions, and applications of the actuator 1204 and/or of other components of the surgical system 1200 as described herein could be implemented as program instructions in the actuation module 1215. For example, the actuation module 1215 could include instructions for operating an actuator of the surgical system 1200 to control a location of the surgical system 1200 and/or to control a location, angle, and/or orientation of a probe head of other housing or assembly of the surgical system 1200.

The detection module 1216 can include instructions for detecting and/or determining one or more properties of a particular portion of biological tissue using the sensor 1206 and/or one or more other components of the surgical system 1200. For example, the detection module 1216 could include instructions to determine a location, color, health state, content, presence of a fluorophore, presence of cancer cells, an electrical impedance, or some other property of the particular portion of the biological tissue. In examples wherein the sensor operates in conjunction with the actuator 1204 (e.g., by detecting light emitted from biological tissue responsive to illumination by the laser 1202 and/or by some other light source that is optically coupled to an optical element controlled by the actuator 1204), the detection module 1216 can include instructions to instruct the actuation module 1215 to control the location of the focus of a beam of illumination (e.g., a beam of fluorophore-exciting illumination) to one or more specified locations, to detect properties of biological tissue located in the one or more specified locations.

The surgical intervention module 1217 can include instructions for planning and/or executing one or more surgical interventions on a biological tissue based on information about the particular portions of biological tissue detected using the sensor 1206. The instructions could include instructions to determine a location, extent, or other properties of an identified target tissue (e.g., an extent of a tumor containing a cancerous target tissue). Instructions of the surgical intervention module 1217 can further include instructions for controlling the laser 1202, actuator 1204, or other elements of the surgical system (e.g., the suction source 1208) to effect one or more surgical interventions (e.g., to ablate a determined region of tissue, to collect occluding matter produced by ablation of tissue, to secure a portion of tissue in a tissue entrance port by applying suction via the tissue entrance port) on the biological tissue. For example, the surgical intervention module 1217 can include instructions for operating the laser 1202 (e.g., controlling a wavelength, energy level, direction or other properties of the light emitted by the laser 1202) according to a determined location, extent, or other properties of an identified target tissue such that the identified target tissue is ablated (e.g., such that a tumor containing cancerous target tissue is ablated).

Some of the program instructions of the actuation module 1215, detection module 1216, and/or surgical intervention module 1217 may, in some examples, be stored in a computer-readable medium and executed by a processor located external to the surgical system 1200. For example, the surgical system 1200 could be configured to illuminate and to receive light from a portion of biological tissue and then transmit related data to a remote server, which may include a mobile device, a personal computer, the cloud, or any other remote system, for further processing (e.g., for the determination of spectrographic content of the received light, for identifying the portion of the surgical environment based on the determined spectrographic content).

User interface 1220 could include indicators, displays, buttons, touchscreens, head-mounted displays, displays of a console of a tele-surgical system, and/or other elements configured to present information about the surgical system 1200 to a user and/or to allow the user to operate the surgical system 1200. Additionally or alternatively, the surgical system 1200 could be configured to communicate with another system (e.g., a cellphone, a tablet, a computer, a remote server) and to present elements of a user interface using the remote system. The user interface 1220 could be disposed proximate to the laser 1202, actuator 1204, sensor 1206, suction source 1208, controller 1210, or other elements of the surgical system 1200 or could be disposed away from other elements of the surgical system 1200 and could further be in wired or wireless communication with the other elements of the surgical system 1200. The user interface 1220 could be configured to allow a user to specify some operation, function, or property of operation of the surgical system 1200. The user interface 1220 could be configured to present information about a biological tissue or other contents of the surgical environment (e.g., a tissue type, a presence of fluorophore) to the user using a display, to present a degree of progress of an ongoing function of the surgical system 1200 (e.g., a degree of progress in ablating biological tissue along a specified trajectory using a laser of the surgical system 1200), to present an image of a biological tissue or other contents of a body cavity using the sensor 1206, or using some other imaging component or sensor, or to present some other information to a user. Other configurations and methods of operation of a user interface 1220 are anticipated.

Communication system(s) 1230 may also be operated by instructions within the program instructions 1214, such as instructions for sending and/or receiving information via a wireless antenna, which may be disposed on or in the surgical system 1200. The communication system(s) 1230 can optionally include one or more oscillators, mixers, frequency injectors, etc. to modulate and/or demodulate information on a carrier frequency to be transmitted and/or received by the antenna. In some examples, the surgical system 1200 is configured to indicate an output from the controller 1210 by transmitting an electromagnetic or other wireless signal according to one or more wireless communications standards (e.g., Bluetooth, WiFi, IRdA, ZigBee, WiMAX, LTE). In some examples, the communication system(s) 1230 could include one or more wired communications interfaces and the surgical system 1200 could be configured to indicate an output from the controller 1210 by operating the one or more wired communications interfaces according to one or more wired communications standards (e.g., USB, FireWire, Ethernet, TCP/IP, RS-232). Further, the communication system(s) 1230 may be configured such that an external system (e.g., a server, a control console of a tele-surgical system, a set of computational resources configured as a cloud computing environment) could receive information from the surgical system 1200 (e.g., imaging or other information about biological tissues in a body cavity, information about the configuration of the surgical system 1200) and send commands to the surgical system 1200 (e.g., directions, locations, angles, powers, or other information specifying properties of a beam of illumination emitted by the surgical probe 1200) in order to perform a surgical intervention on a person.

The computer readable data storage 1212 may further contain other data or information, such as medical and health history of a patient whose biological tissue is being imaged or otherwise interacted with by the surgical system 1200, that may be useful in tracking or otherwise interacting with a biological tissue or other environment of interest. Further, the computer readable data storage 1212 may contain data corresponding to imaging information about a biological tissue or other environment of interest. The computer readable data storage 1212 may contain calibration data corresponding to a configuration of the surgical system 1200, a calibration object, or some other information. Calibration, model, imaging, and/or other data may also be generated by a remote server and transmitted to the surgical system 1200 via communication system(s) 1230.

In some examples, the collected calibration and/or model data, stored information about operation of the surgical system 1200 (e.g., information about past uses and/or operations of the surgical system, information about identification of biological tissue or other contents of a surgical environment performed using the surgical system 1200), health state information (e.g., health state of biological tissue) detected by the surgical system 1200 and other usage or other information may additionally be input to a cloud network (e.g., using the communications system(s) 1230) and be made available for download by users having sufficient permissions (e.g., a surgeon tasked with reviewing the outcome of a surgical intervention wholly or partially effected using the surgical system 1200). Other analyses may also be performed on the collected data, such as physiological parameter data and health state information, in the cloud computing network and be made available for download by physicians or clinicians.

Further, physiological parameter and health state data from individuals or populations of device users may be used by physicians or clinicians in monitoring outcomes of a surgical intervention or other treatment. For example, high-density, real-time data may be collected from a population of device users who have experienced a surgical intervention implemented using the surgical system 1200 to assess the safety and efficacy of the surgical intervention. Such data may also be used on an individual level to assess a particular patient's response to a surgical intervention or therapy. Based on this data, a physician or clinician may be able to tailor a future surgical intervention or other treatment to suit an individual's needs.

VII. EXAMPLE METHODS

Figure 13:
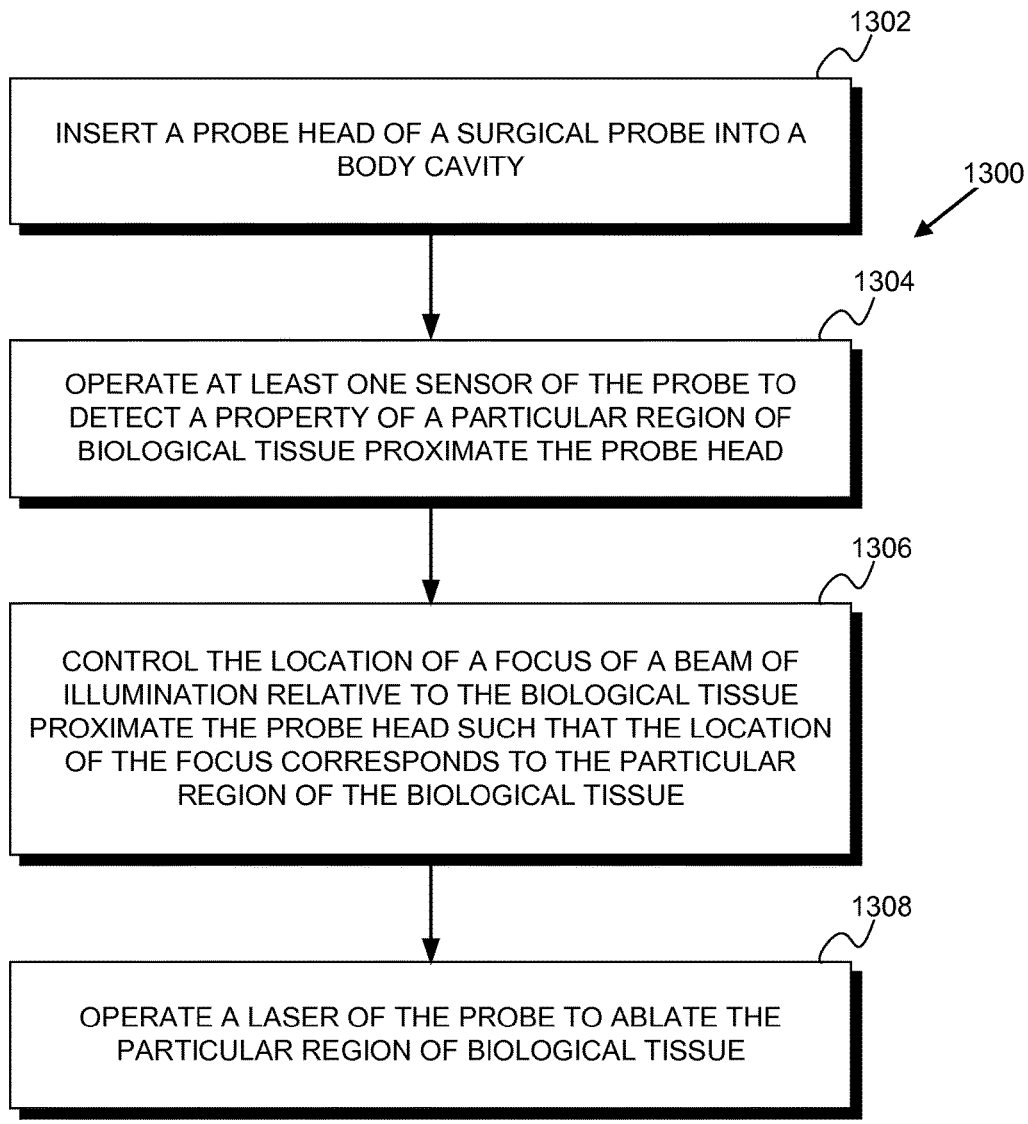
FIG. 13 is a flowchart of an example method.

FIG. 13 is a flowchart of an example method 1300 for operating elements of a surgical probe to perform functions and/or applications of the surgical probe. The surgical probe includes a probe head configured to be inserted into a body cavity. The surgical probe additionally includes a laser configured to emit a beam of illumination capable of ablating biological tissue proximate the probe head and at least one optical element (e.g., a mirror, a lens) optically coupled to the laser. The surgical probe additionally includes an actuator configured to adjust, affect, or otherwise control the at least one optical element that is coupled to the laser. The surgical probe additionally includes a controller configured to control a location of a focus of the beam of illumination relative to the biological tissue proximate the probe head by controlling at least one of the actuator or applied suction. The surgical probe additionally includes at least one sensor configured to detect a property of a the particular region of biological tissue proximate to the probe head.

The method 1300 includes inserting the probe head into a body cavity (1302). This could include manually inserting (e.g., by a surgeon) the probe head into the body cavity. The location of the probe head in the body cavity could be maintained by the surgeon (e.g., while receiving imaging or other placement feedback from a display or by other means) and/or could be affixed by a surgical frame or other means. In some examples, the probe head could be part of a robotic surgical system, and insertion of the probe head could be performed by operation of one or more actuators of the robotic surgical system to extend the probe head through an incision or by some other route into the body cavity. In some examples, inserting the probe head into a body cavity (1302) could include installing a trocar through one or more overlying tissues (e.g., skin, muscle, peritoneum) into the body cavity, and inserting the probe head into the body cavity through the trocar.

The method 1300 additionally includes operating at least one sensor of the surgical probe to detect a property of a particular region of biological tissue proximate to the probe head (1304). This could include operating one or more light sensors (e.g., sensors of visible light, infrared radiation, and/or ultraviolet radiation), mechanical sensors (e.g., load cells, displacement sensors), acoustical sensors (e.g., ultrasonic transducers), temperature sensors, electrodes, pH sensors, chemical sensors, or some other sensors to detect a color, health state, optical spectrum, electrical impedance, electrical potential, presence of an analyte (e.g., cancer cells), or some other property of the particular portion of tissue.

Operating at least one sensor of the surgical probe to detect a property of a particular region of tissue (1304) could include emitting an energy toward (e.g., illuminating) the particular region of tissue (e.g., using the actuator and/or optical elements of the surgical probe). For example, the particular region of tissue could be illuminated with light at an excitation wavelength of a fluorophore (e.g., a fluorophore configured to selectively interact with an analyte in the biological tissue) and light or other energy responsively emitted from the particular region of tissue (e.g., light at an emission wavelength of the fluorophore) could be detected to detect and/or determine the presence, concentration, binding state, or other information about the fluorophore in the biological tissue. In some examples, detecting a property of the particular region of tissue could include illuminating the particular region of biological tissue with further beams of illumination at a plurality of different wavelengths and determining spectrographic content (e.g., features or other information about an absorption, emission, excitation, reflection, or other spectrum) of light received from the particular region of biological tissue in response to illumination by the further beams of illumination. In some examples, a location of the particular portion of tissue could be determined (e.g., through triangulation, through time-of-flight measurement of optical and/or acoustical energies emitted toward and received from the particular portion of tissue). Other properties of the particular portion of tissue could be determined by additional or alternative means.

The method 1300 additionally includes controlling the location of a focus of the beam of illumination relative to the biological tissue proximate the probe head such that the location of the focus corresponds to the particular region of the biological tissue (1306). This could include controlling an actuator of the probe to adjust the at least one optical element of the probe to control the location of a focus of the beam of illumination. For example, one or more actuators could be controlled to adjust, affect, or otherwise control an angle, orientation, location, or other properties of one or more optical elements (e.g., mirrors, lenses, diffraction gratings, filters, optical fibers, or other optical elements). In some examples, this (1306) could include applying suction. For example, suction could be applied via a tissue entrance port of the probe head to secure a portion of biological tissue at a specified location relative to the probe head and/or relative to the location of a focus of the beam of illumination.

Additionally or alternatively, the method 1300 could include one or more actuators to control the location, angle, and/or orientation of the probe head to control the location of the focus of the beam of illumination. In some examples, the sensor could be configured to detect the property of the particular region of biological tissue using one or more of the optical elements of the probe that are actuated by the actuator. In such examples, operating an actuator of the probe to control the at least one optical element of the probe to control the location of a focus of the beam of illumination to correspond to the location of the particular region of biological tissue (1306) could be performed before detecting the property of the particular portion of biological tissue, such that a correspondence between the particular portion of tissue detected by the sensor and the location of the focus of the beam of illumination could be assured. The method 1300 additionally includes operating the laser to ablate the particular region of biological tissue (1308). This could include determining, based on the property detected using the sensor, that the particular portion of biological tissue contains a target (e.g., cancer cells, a cyst, an infection) and responsively operating the laser to ablate the particular region of biological tissue (1308). Operating the laser to ablate the particular region of biological tissue (1308) could include emitting a beam of illumination to ablate, dissect, cauterize, or otherwise damage or destroy the target tissue. Emitting the beam of illumination from the laser could include operating a 2 micron laser, $CO_2$ laser, an excimer laser, or some other variety of laser configured to apply energy to biological tissue sufficient to ablate or otherwise modify the biological tissue.

The method 1300 could include additional steps. For example, the method could include applying suction, via a collection port of the surgical probe, to collect occluding material (e.g., smoke, particulates, blood) from on or near the probe head that is produced by ablation of biological tissue by the beam of illumination. This operation could be performed responsive to a determination and/or detection (e.g., using the sensor) that material produced by ablation of biological tissue by the beam of illumination is present proximate to the probe head. In some examples, the method 1300 could include operating the surgical probe to cut biological tissue along a specified surface (e.g., by rotating the probe head while operating the laser to emit a tissue-ablating beam of illumination) that at least partially encloses a target. The method 1300 could further include removing the target by cutting the biological tissue along an additional specified surface that intersects with the first specified surface or according to some other method.

The method 1300 could include other additional steps or elements. The method 1300 could include any additional steps, or could include details of implementation of the listed steps 1302, 1304, 1306, 1308 or of other additional steps, as described herein in relation to the operation of a surgical probe. Additional and alternative steps of the method 1300 are anticipated.

In some examples, the surgical environment, body cavity, or other enclosed or semi-enclosed cavity of space described in relation to the method 1300 above could contain a biological tissue of a human body. For example, the environment could contain a tissue that has been determined to include a tumor that could be resected, ablated, or otherwise removed to change and/or affect a health state of the human body. Other examples of surgical environments, body cavities, biological tissues, surgical interventions, surgical instruments, foreign bodies, methods of operating a surgical probes, configurations of surgical probes, and other elements are anticipated.

VIII. CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in which embodiments discussed herein collect personal information about users, or may make use of personal information, the users may be provided with an opportunity to control whether programs or features collect user information (e.g., information about a user's medical history, information about a surgical intervention performed on the user, information about biological tissues of a user, a user's preferences, or a user's current location), or to control whether and/or how to receive content from a content server (e.g., a profile of power to ablate a tissue applied using a laser) that may be relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a hospital, hospital system, city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Moreover, it is particularly noted that while devices, systems, methods, and other embodiments are described herein by way of example as being employed to image and/or manipulate biological environments (e.g., tissues) of a human body, it is noted that the disclosed devices, systems, and methods can be applied in other contexts as well. For example, imaging and/or ablation systems configured as disclosed herein may be included as part of other surgical and/or medical imaging apparatus. In some contexts, such a system could be operated to detect one or more properties of a tissue or other element of a human body, possibly in concert with other medical imaging or other sensor apparatus. In another example, a system could be configured to image and/or ablate specified elements and/or regions of a non-tissue element of a human body. For example, the imaging system could be configured and/or applied to image specified regions of an implantable device (e.g., a stent, an artificial joint, a pacemaker) to control the effecting of a desired change in the implantable device (e.g., to section the device, to weld an element of the device, to activate an element of the device, to trim an element (e.g., an electrode) of the device).

In other examples, devices, systems, and methods disclosed herein may be applied to image and/or ablate regions of environments that are not in or on a human body. For example, systems disclosed herein may be included in systems used to image and/or ablate specified regions (e.g., tissues) of an animal. In another example, devices, systems, and methods disclosed herein may be applied to image and/or ablate regions of an industrial environment or a work element of an industrial process, such as a work element in a laser cutting or shaping process.

Additionally, while various aspects and embodiments have been disclosed herein, other aspects and embodiments will be apparent to those skilled in the art. The various aspects and embodiments disclosed herein are included for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A system comprising:
a surgical probe, wherein the surgical probe comprises a probe head configured to be inserted into a body cavity;
a laser, wherein the laser is configured to emit a beam of illumination capable of ablating a biological tissue proximate the probe head;
a tissue entrance port in the probe head through which suction can be applied to secure a portion of biological tissue, wherein the portion of biological tissue interacts with the laser inside the probe head;
a collection port through which suction can be applied to collect occluding material produced by ablation of the biological tissue by the beam of illumination;
at least one optical element, wherein the at least one optical element is optically coupled to the laser;
an actuator coupled to the at least one optical element;
at least one sensor disposed within the probe head, wherein the at least one sensor is configured to detect a property of the biological tissue proximate to the probe head; and
a computing device programmed to perform operations comprising:
controlling a location of a focus of the beam of illumination relative to the biological tissue proximate the probe head by controlling at least one of the actuator or applied suction;
determining, using the at least one sensor, whether occluding material is present proximate to the probe head; and
responsive to a determination that occluding material is present proximate to the probe head, applying suction, via the collection port, to collect the occluding material.

2. The system of claim 1, further comprising:
a further light source, wherein the further light source is configured to emit a further beam of illumination, wherein the further light source is controllable to emit the further beam of illumination at any of a plurality of different wavelengths, wherein the at least one optical element is optically coupled to the further light source such that the location of a focus of the further beam of illumination is substantially the same as the location of the focus of the beam of illumination emitted by the laser, and wherein the at least one sensor is configured to receive light emitted from the biological tissue proximate to the probe head in response to illumination by the further beam of illumination.

3. The system of claim 1, wherein the at least one optical element comprises a mirror, wherein an axial location of the mirror along a longitudinal axis of the surgical probe is adjustable by the actuator, such that the actuator can adjust a location of the beam of illumination relative to the probe head by adjusting the axial location of the mirror.

4. The system of claim 1, wherein the at least one optical element comprises a lens, wherein a location of the lens along a path of the beam of illumination is adjustable by the actuator, such that the actuator can adjust a distance between the location of the focus of the beam of illumination and the probe head by adjusting the location of the lens along the path of the beam of illumination.

5. The system of claim 1, wherein the at least one optical element comprises a mirror, wherein an angle of the mirror is adjustable by the actuator, such that the actuator can adjust an angle of the beam of illumination relative to the probe head by adjusting the angle of the mirror.

6. The system of claim 1, further comprising:
a window, wherein the beam of illumination is emitted from the probe head via the window; and
a scraper, wherein the scraper is configured to remove occluding matter from an external surface of the window.

7. The system of claim 1, further comprising:
a further light source, wherein the further light source is configured to illuminate a particular region of the biological tissue with light at a wavelength corresponding to an excitation wavelength of a fluorophore, wherein the at least one sensor is configured to detect a property of the biological tissue by detecting light at an emission wavelength of the fluorophore that is emitted from the particular region in response to illumination by the further light source.

8. The system of claim 1, further comprising:
a further light source, wherein the further light source is configured to illuminate a particular region of the biological tissue, wherein the at least one sensor comprises a camera configured to image an area of the biological tissue that includes the particular region.

9. The system of claim 1, wherein the computing device is programmed to control the location of the focus of the beam of illumination relative to the biological tissue proximate the probe head at least in part by controlling suction applied through the tissue entrance port.

10. The system of claim 1, wherein the surgical probe further comprises a tubular support and an articulation, wherein the articulation controls an angle between the probe head and the tubular support.

11. A method comprising:
inserting a probe head of a surgical probe into a body cavity, wherein the surgical probe comprises:
a laser, wherein the laser is configured to emit a beam of illumination capable of ablating biological tissue proximate the probe head;
at least one optical element, wherein the at least one optical element is optically coupled to the laser;
an actuator coupled to the at least one optical element;
a tissue entrance port in the probe head through which suction can be applied to secure a portion of the biological tissue, wherein the portion of biological tissue interacts with the laser inside the probe head;
a collection port through which suction can be applied to collect occluding material produced by ablation of the biological tissue by the beam of illumination and
at least one sensor disposed within the probe head, wherein the at least one sensor is configured to detect a property of the biological tissue proximate to the probe head;
operating the at least one sensor to detect a property of a particular region of the biological tissue proximate to the probe head;
controlling a location of a focus of the beam of illumination relative to the biological tissue proximate the probe head by controlling at least one of the actuator or applied suction such that the location of the focus of the beam of illumination corresponds to the particular region of the biological tissue;

operating the laser to ablate the particular region of the biological tissue;

determining, using the at least one sensor, whether occluding material is present proximate to the probe head; and responsive to a determination that occluding material is present proximate to the probe head, applying suction, via the collection port, to collect the occluding material.

12. The method of claim 11, wherein the surgical probe further comprises a further light source, wherein the further light source is configured to emit a further beam of illumination, wherein the further light source is controllable to emit the further beam of illumination at any of a plurality of different wavelengths, wherein the at least one optical element is optically coupled to the further light source such that the location of a focus of the further beam of illumination is substantially the same as the location of the focus of the beam of illumination emitted by the laser, and wherein the at least one sensor is configured to receive light emitted from the biological tissue proximate to the probe head in response to illumination by the further beam of illumination, and wherein operating the at least one sensor to detect a property of a particular region of the biological tissue comprises:

operating the further light source to illuminate the particular region of the biological tissue;

operating the at least one sensor to receive light emitted from the particular region of the biological tissue in response to illumination by the further beam of illumination; and determining a spectrographic content of the received light.

13. The method of claim 11, wherein the surgical probe further comprises a further light source configured to emit light at a wavelength corresponding to an excitation wavelength of a fluorophore, and further comprising:

illuminating the particular region of the biological tissue proximate the probe head using the further light source, wherein operating the at least one sensor to detect a property of the particular region comprises detecting light at an emission wavelength of the fluorophore emitted from the particular region in response to illumination by the further light source; and determining that the particular region contains the fluorophore based on the detected light from the particular region.

14. The method of claim 11, wherein the surgical probe further comprises a further light source configured to illuminate the particular region, wherein the at least one sensor comprises a camera configured to image an area of the biological tissue that includes the particular region, and further comprising:

determining the location of the particular region relative to the probe head based on an image generated by the camera.

15. The method of claim 11, further comprising:

controlling the location of a focus of the beam of illumination relative to the biological tissue proximate the probe head at least in part by controlling suction applied through the tissue entrance port.

16. The method of claim 11, further comprising controlling the location of focus of the beam of illumination relative to the biological tissue proximate the probe head by adjusting at least one of an angle of the probe head relative to the biological tissue proximate the probe head or a location of the probe head along a longitudinal axis of the surgical probe relative to the biological tissue proximate the probe head.

17. The method of claim 11 further comprising:

positioning the probe head proximate to a target within the biological tissue proximate the probe head;

rotating the probe head;

while the probe head is rotating, adjusting the at least one optical element via the actuator in conjunction with the laser to cut the biological tissue along a specified surface that at least partially encloses the target; and extracting the target, wherein extracting the target comprises:

dissecting the biological tissue along a dissection surface that fully encloses the target, wherein the dissection surface comprises the specified surface; and removing the biological tissue contained within the dissection surface from the body cavity.

* * * * *

UNITED STATES PATENT AND TRADEMARK OFFICE
CERTIFICATE OF CORRECTION

PATENT NO. : 10,092,355 B1
APPLICATION NO. : 14/550560
DATED : October 9, 2018
INVENTOR(S) : Blake Hannaford et al.

Page 1 of 1

It is certified that error appears in the above-identified patent and that said Letters Patent is hereby corrected as shown below:

On the Title Page

Item (72):
In Line 1 of the Inventors: delete "Eugene"
In Line 3 of the Inventors: delete "Jöelle" and insert --Joëlle--

Signed and Sealed this
Twenty-eighth Day of January, 2020

Andrei Iancu
*Director of the United States Patent and Trademark Office*